US010605698B2

(12) United States Patent
Held et al.

(10) Patent No.: US 10,605,698 B2
(45) Date of Patent: Mar. 31, 2020

(54) METHOD AND APPARATUS FOR CHECKING TYRES

(71) Applicant: PIRELLI TYRE S.P.A., Milan (IT)

(72) Inventors: Alessandro Held, Milan (IT); Vincenzo Boffa, Milan (IT); Daniele Pecoraro, Milan (IT); Valeriano Ballardini, Imola (IT); Josef Engelsberger, Neubeuern (DE); Bernd Leitner, Neubeuern (DE)

(73) Assignee: PIRELLI TYRE S.P.A., Milan (IT)

( * ) Notice: Subject to any disclaimer, the term of this patent is extended or adjusted under 35 U.S.C. 154(b) by 26 days.

(21) Appl. No.: 15/780,602

(22) PCT Filed: Dec. 16, 2016

(86) PCT No.: PCT/IB2016/057712
§ 371 (c)(1),
(2) Date: May 31, 2018

(87) PCT Pub. No.: WO2017/103873
PCT Pub. Date: Jun. 22, 2017

(65) Prior Publication Data
US 2019/0086293 A1 Mar. 21, 2019

(30) Foreign Application Priority Data
Dec. 16, 2015 (IT) .............................. UB2015A9501

(51) Int. Cl.
G01N 21/954 (2006.01)
G01M 17/02 (2006.01)
(Continued)

(52) U.S. Cl.
CPC ...... G01M 17/027 (2013.01); G01N 21/8806 (2013.01); G01N 21/8851 (2013.01);
(Continued)

(58) Field of Classification Search
CPC .. G01N 21/954; G01N 21/8851; G01N 21/95; G01N 21/8806; G01N 2021/8887; G01M 17/027
(Continued)

(56) References Cited

U.S. PATENT DOCUMENTS 6,327,374 B1 12/2001 Piironen et al.
6,840,097 B1 1/2005 Huber et al.
(Continued)

FOREIGN PATENT DOCUMENTS

DE 4231578 A1 3/1994
EP 1030173 A1 8/2000
(Continued)

OTHER PUBLICATIONS

International Search Report issued for International Patent Application No. PCT/IB2016/057712, filed Dec. 16, 2016 on behalf of Pirelli Tyre S.P.A. dated Mar. 30, 2017. 4 pages.
(Continued)

Primary Examiner — Hoa Q Pham
(74) Attorney, Agent, or Firm — Steinfl + Bruno LLP

(57) ABSTRACT

Method for checking a tyre. The method includes associating first and second independent light sources with a camera, applying a first force against a first surface portion of the tyre to generate a first deformed surface portion, and illuminating the first deformed surface portion with a first light radiation emitted by the first light source while keeping the second light source deactivated. A first image of the first deformed surface portion is then acquired by the camera. The first force is removed and a second surface portion partially distinct from the first surface portion is illuminated with a second light radiation emitted by the second light source without deforming the second surface portion. A second image of the second surface portion is then acquired by the (Continued)

camera. The first and second images are processed for detection of possible defects in the first and second surface portions.

26 Claims, 11 Drawing Sheets

(51) Int. Cl.
*G01N 21/88* (2006.01)
*G01N 21/95* (2006.01)
*H04N 5/225* (2006.01)

(52) U.S. Cl.
CPC ..... *G01N 21/95* (2013.01); *G01N 2021/8812* (2013.01); *H04N 5/2256* (2013.01)

(58) Field of Classification Search
USPC .......................... 356/237.1–237.5, 601–623
See application file for complete search history.

(56) References Cited

U.S. PATENT DOCUMENTS

| | | | |
|---|---|---|---|
| 7,187,437 B2 | 3/2007 | Shaw et al. | |
| 7,421,108 B2 | 9/2008 | Kaneko et al. | |
| 7,466,430 B2 | 12/2008 | Braghiroli | |
| 8,284,393 B2* | 10/2012 | Takahashi | G01B 11/25 356/237.1 |
| 9,175,952 B2 | 11/2015 | Mizutani et al. | |
| 9,719,944 B2* | 8/2017 | Boffa | G01M 17/027 |
| 2010/0002244 A1* | 1/2010 | Iino | G01M 17/027 356/601 |
| 2011/0018999 A1 | 1/2011 | Joly et al. | |
| 2011/0288814 A1 | 11/2011 | Mizutani et al. | |
| 2012/0134656 A1 | 5/2012 | Mizukusa et al. | |
| 2014/0373614 A1 | 12/2014 | Steinbichler et al. | |
| 2016/0377556 A1* | 12/2016 | Boffa | G01M 17/027 356/237.2 |
| 2018/0364134 A1* | 12/2018 | Held | G01M 17/027 |
| 2018/0372590 A1 | 12/2018 | Held et al. | |
| 2018/0372592 A1 | 12/2018 | Held et al. | |
| 2019/0017902 A1 | 1/2019 | Held et al. | |
| 2019/0086293 A1* | 3/2019 | Held | G01N 21/8806 |
| 2019/0318466 A1* | 10/2019 | Ghidotti Piovan | G06T 7/001 |

FOREIGN PATENT DOCUMENTS

| | | |
|---|---|---|
| EP | 1120640 A1 | 8/2001 |
| EP | 2078955 A1 | 7/2009 |
| EP | 2322899 A1 | 5/2011 |
| WO | 2015/004587 A1 | 1/2015 |
| WO | 2015/079370 A1 | 6/2015 |
| WO | 2017/115290 A1 | 7/2017 |
| WO | 2017/115300 A1 | 7/2017 |
| WO | 2017/141094 A1 | 8/2017 |

OTHER PUBLICATIONS

Written Opinion issued for International Patent Application No. PCT/IB2016/057712, filed Dec. 16, 2016 on behalf of Pirelli Tyre S.P.A. dated Mar. 30, 2017. 6 pages.
International Search Report for International Application No. PCT/IB2016/058038 filed Dec. 28, 2016 on behalf of Pirelli Tyre S.P.A. dated May 11, 2017. 3 pages.
International Search Report for International Patent Application No. PCT/IB2016/058036 filed Dec. 28, 2016 on behalf of Pirelli Tyre S.P.A. dated Jul. 21, 2017. 3 pages.
International Search Report for International Patent Application No. PCT/IB2016/058052 filed Dec. 28, 2016 on behalf of Pirelli Tyre S.P.A. dated Jun. 16, 2017. 3 pages.
Written Opinion for International Application No. PCT/IB2016/058038 filed Dec. 28, 2016 on behalf of Pirelli Tyre S.P.A. dated May 11, 2017. 6 pages.
Written Opinion for International Patent Application No. PCT/IB2016/058036 filed Dec. 28, 2016 on behalf of Pirelli Tyre S.P.A. dated Jul. 21, 2017. 7 pages.
Written Opinion for International Patent Application No. PCT/IB2016/058052 filed Dec. 28, 2016 on behalf of Pirelli Tyre S.P.A. dated Jun. 16, 2017. 8 pages.
Non-Final Office Action for U.S. Appl. No. 16/066,264, filed Jun. 26, 2018, on behalf of Pirelli, Tyre S.P.A. dated Jan. 16, 2019. 8 pages.

* cited by examiner

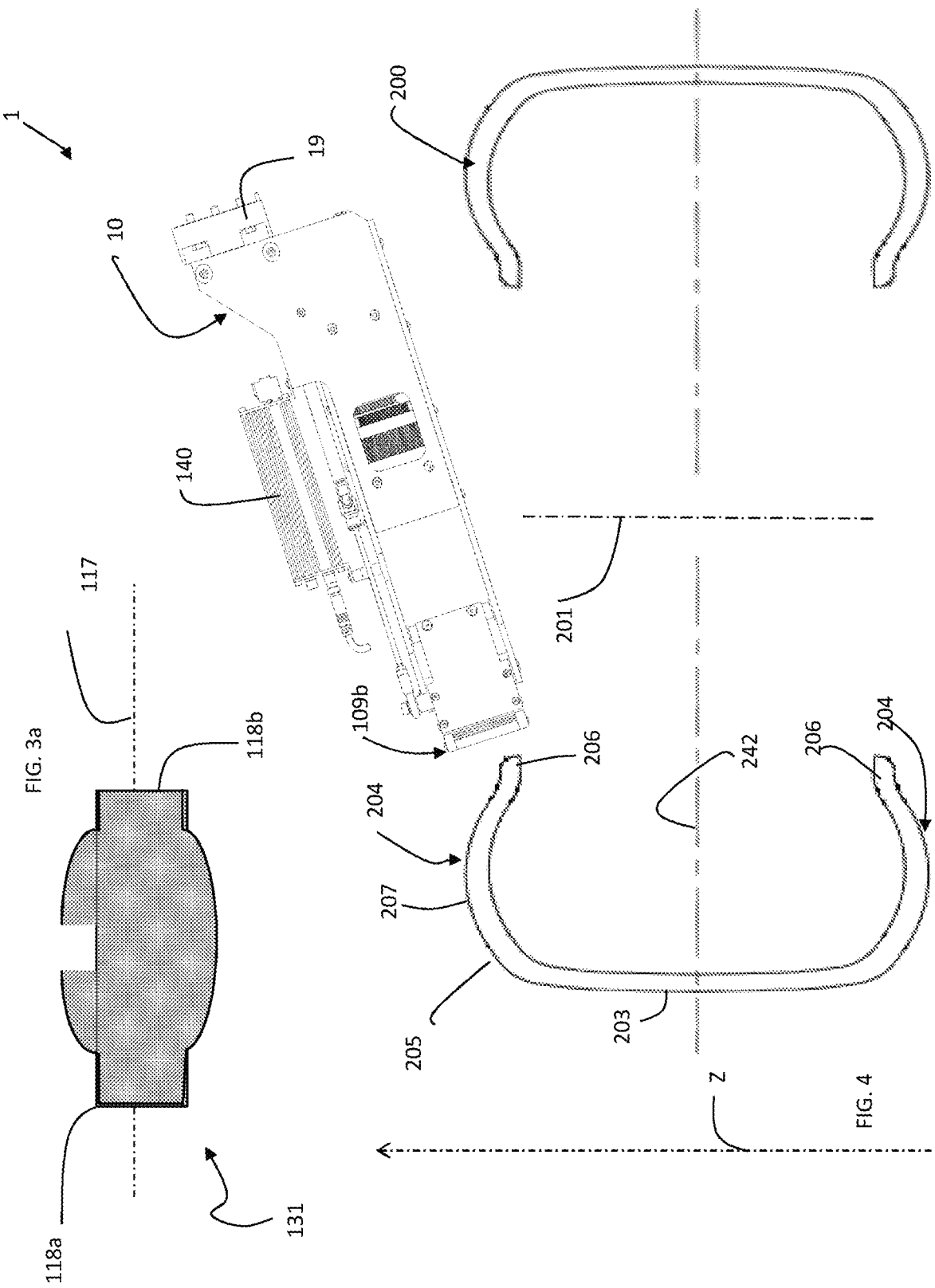

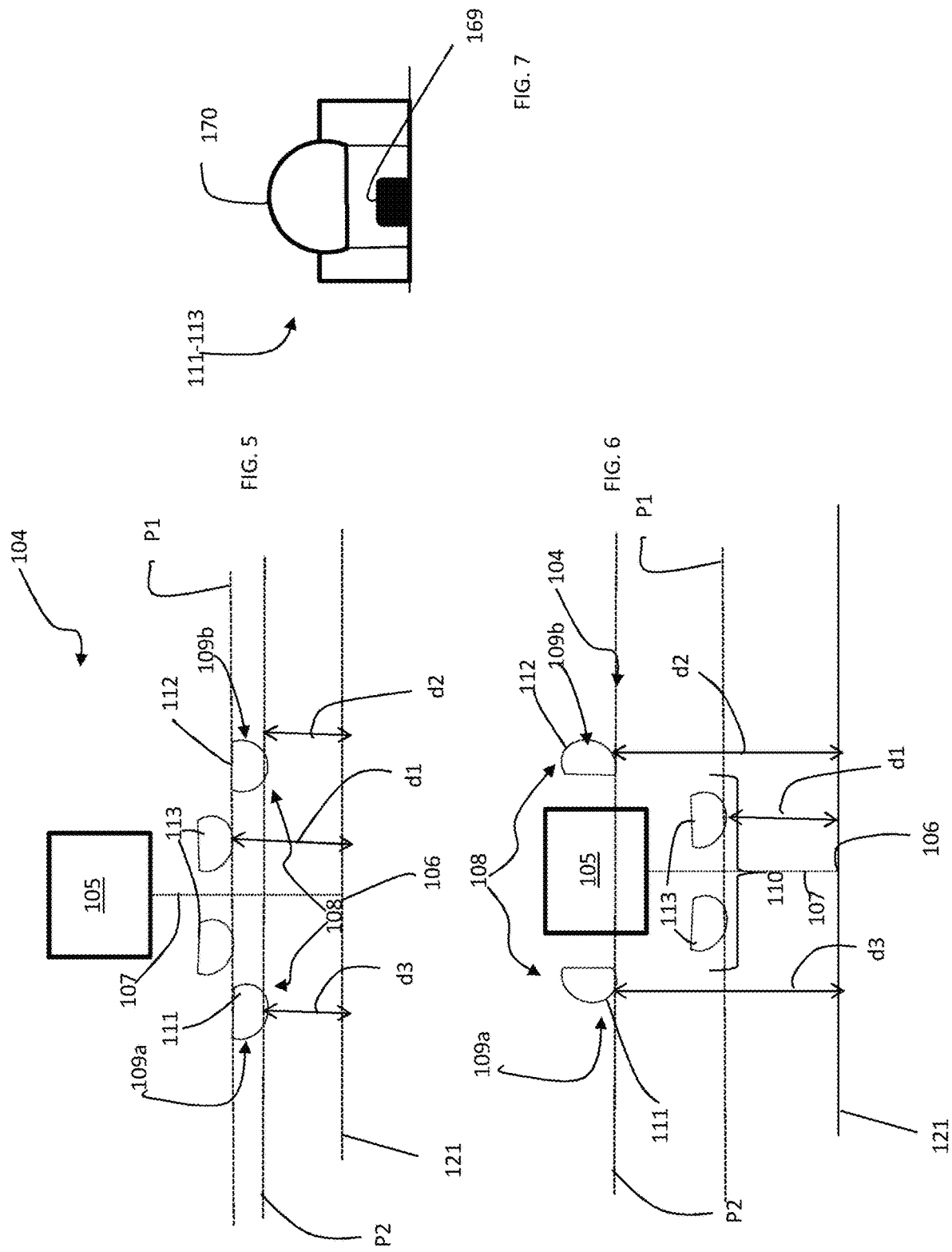

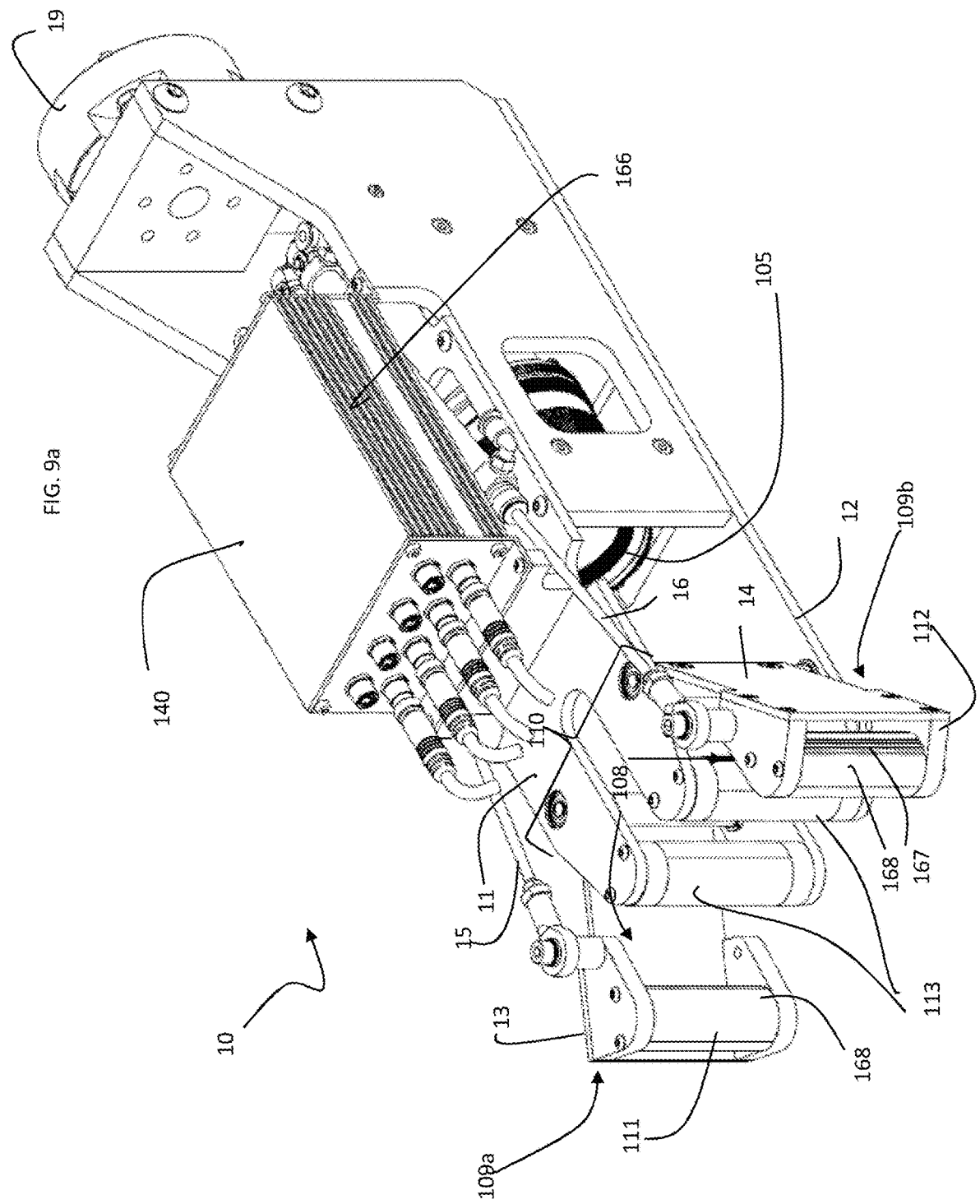

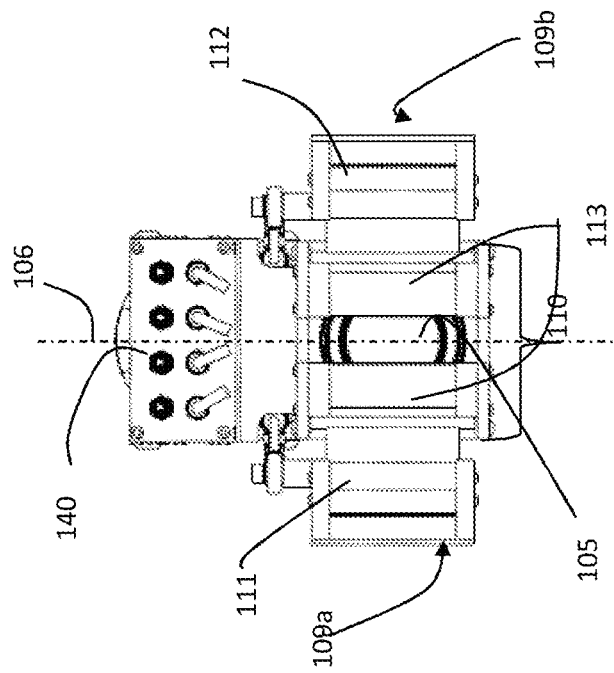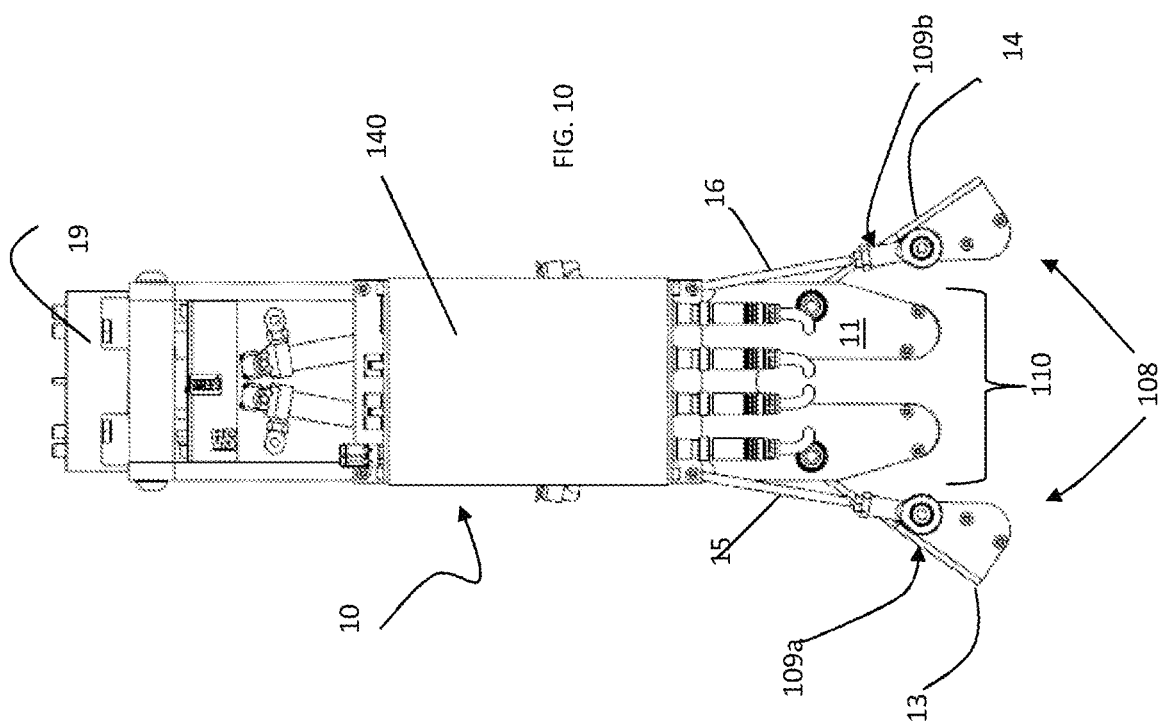

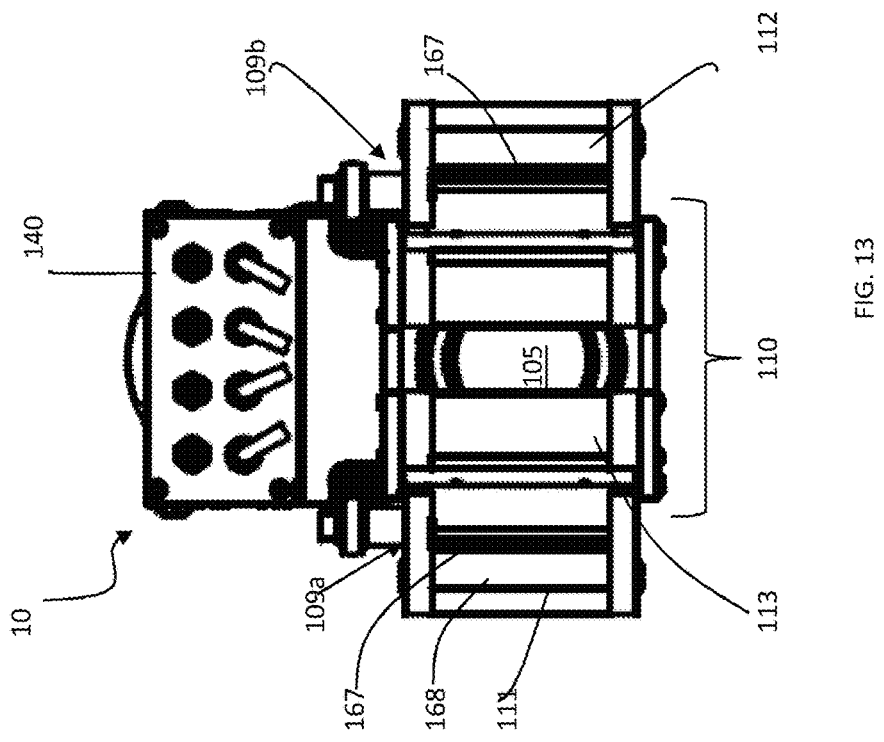
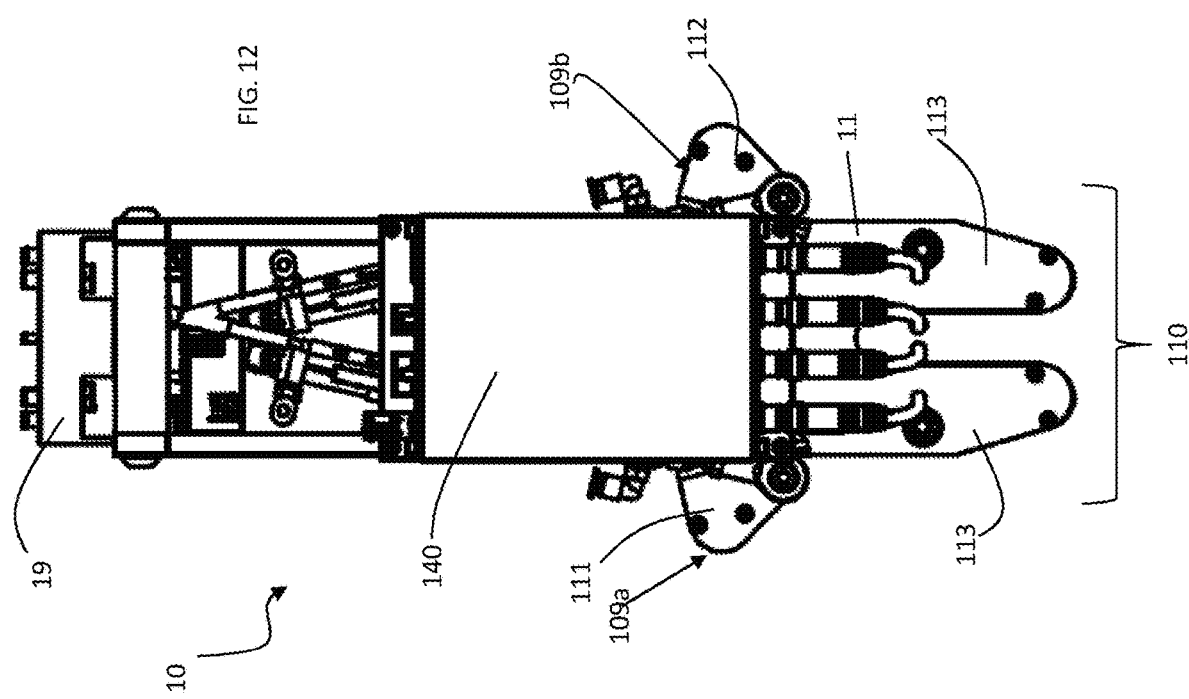

METHOD AND APPARATUS FOR CHECKING TYRES

CROSS REFERENCE TO RELATED APPLICATIONS

The present application is the U.S. National Stage of International Patent Application No. PCT/IB2016/057712 filed on Dec. 16, 2016 which, in turn, claims priority to Italian Application No. UB2015A009501 filed on Dec. 16, 2015.

The present invention relates to a method and an apparatus for checking tyres, for example in a tyre production line, in particular a method and apparatus for checking for the possible presence of defects on, or close to, the surface of a tyre, more in particular on, or close to, the inner and/or outer surface of the side walls of a tyre.

Typically, a tyre has a substantially toroidal structure about a rotation axis thereof during operation, and has an axial mid-plane perpendicular to the rotation axis, said plane typically being a plane of substantial geometric symmetry, ignoring possible minor asymmetries, such as the tread pattern and/or the internal structure.

Two portions of the tyre are identified here: the crown and the side walls. The crown comprises the tread band, the belt and the corresponding portion of carcass structure radially inside them.

The term "side wall" is meant to indicate one of the two portions of the tyre facing one another and that extend radially on opposite sides of the crown up to the beads, i.e. up to the two radially inner end edges of the tyre, having circular extension substantially perpendicular to the rotation axis; said beads being intended to each couple with a respective mounting rim. Each side wall thus comprises a corresponding portion of carcass structure and, in a position axially outside of it, a portion made of suitable elastomeric material, generally called 'sidewall'.

Typically, the carcass structure comprises at least one carcass ply having respectively opposite end edges engaged with respective annular reinforcing structures, generally called "bead wires", integrated in the areas identified above with the name beads. In "tubeless" tyres, the carcass ply is entirely coated with a layer of elastomeric material preferably butyl-based, usually called "liner" having excellent characteristics of impermeability to air and extending from one bead to another.

The structure of a side wall is also meant to entirely include the so-called "shoulder", i.e. the portion of the tyre for joining between the crown and the radially inner portion of the side wall (in other words, the two shoulders correspond to the two radially and axially outer circular 'edges' of the tyre). The shoulder has circular extension substantially perpendicular to the rotation axis.

The term "tyre" is meant to indicate the finished tyre, i.e. after the moulding and vulcanisation steps following the building step.

The term component of the tyre is meant to indicate any element that performs a function, or a portion thereof.

The terms outer or inner surface of the tyre, are respectively meant to indicate the surface that remains visible after the coupling of the tyre with its mounting rim and that which is no longer visible after said coupling.

The terms "optical", "luminous" and similar refer to an electromagnetic radiation used that has at least one portion of the spectrum falling within a widened range of the optical band, and not necessarily falling strictly within the optical band (in other words 400-700 nm), for example such a widened range of the optical band can extend from ultraviolet to infrared (for example wavelengths comprised between about 100 nm and about 1 µm).

In the present application a ray model of light radiation is adopted, i.e. it is presumed that light radiation incident on a point of a surface and generated by a non-pointed source (in which case there would be a single ray) corresponds to a set of light rays incident on the point and having rectilinear propagation direction that connects each point of the source with said point of the surface, where each of such rays has an associated fraction of the total light power incident on the point. The terms "light" and "light radiation", unless specified otherwise, are used interchangeably.

The term "directional light radiation" incident at a point of a surface is meant to indicate light radiation for which there is a solid angle having the point as vertex and amplitude less than or equal to $\pi/8$ steradians in which at least 75% of the total light power, preferably at least 90%, more preferably the entire light power falls.

The term "diffused light radiation" is meant to indicate a non-directional light radiation.

The term "grazing light radiation" incident at a point of a surface is meant to indicate a light radiation in which at least 75% of the total light power thereof incident on the point of the surface forms an angle of incidence less than or equal to 60° with a plane tangent to the surface at each said point.

The term "image" or synonymously "digital image" is meant to indicate in general a dataset, typically contained in a computer file, in which each coordinate (typically two-dimensional) of a finite set (typically two-dimensional and of the matrix type, i.e. N rows×M columns) of spatial coordinates (each typically corresponding to a pixel) is associated with a corresponding set of numeric values (which can be representative of magnitudes of a different type). For example, in monochromatic images (like those on the 'grayscale') such as set of values coincides with a single value in a finite scale (typically with 256 levels or tones), such a value for example being representative of the level of luminosity (or intensity) of the respective spatial coordinate when visualised, whereas in colour images the set of values represents the level of luminosity of multiple colours, or channels, typically the primary colours (for example in the RGB colour model red, green and blue, whereas in the CMYK colour model cyan, magenta, yellow and black). The term 'image' does not necessarily imply the actual visualisation thereof.

Every reference to a specific "digital image" (for example to a two-dimensional digital image initially acquired on the tyre) more generally covers any digital image that can be obtained through one or more digital processing operations of said specific digital image (like for example filtering, equalisation, "thresholding", morphological transformations—"opening", etc., —gradient calculations, "smoothing", etc.).

The term "linear surface portion" is meant to indicate a surface portion having one dimension much larger than the other dimension perpendicular to it, typically greater by at least two orders of magnitude. The smaller dimension of the linear surface portion is typically smaller than or equal to 0.1 mm.

The term "linear image" is meant to indicate a digital image having a much greater number of columns of pixels than the number of rows, typically greater by at least two orders of magnitude. Typically, the number of rows is between 1 and 4 and the number of columns is more than 1000. The term "rows" and "columns" are used conventionally and are interchangeable.

The term "cycle time" within a production line comprising at least one work station, preferably a plurality of work stations, and inserted in a plant for producing tyres is meant to indicate, under normal operating conditions, the maximum transit time for a tyre being manufactured to pass through a work station in which at least one portion of a component of the tyre itself is built. For example, the cycle time can be comprised between about 20 and about 120 seconds.

In processes for producing and building tyres for vehicle wheels there is a need to carry out quality controls on the products made, with the purpose of avoiding tyres that are defective or in any case outside of the design specifications from being able to be released onto the market, and/or of progressively adjusting the apparatuses and machinery used, so as to improve and optimise the performance of the operations carried out in the production process.

Such quality controls include for example those carried out by human operators who spend a predetermined time period, for example comprised between 30 s and 60 s, carrying out a visual and tactile examination of the tyre; if, in light of his/her experience and sensitivity, the operator suspects that the tyre does not meet certain quality standards, the tyre itself is subjected to further checks, through a more detailed human check and/or suitable apparatuses, in order to more deeply evaluate possible structural and/or quality deficiencies. WO 2015/004587 to the same Applicant shows a method and relative apparatus, for checking tyres in a production line, comprising: providing a tyre to be checked; elastically deforming a portion of side wall of the tyre through a compression force on an outer contact surface of the portion of side wall, the compression force having an axial direction and going towards the plane of the middle line; illuminating an inner and/or outer surface of the portion of side wall and detecting an image of the surface illuminated; generating a control signal representative of the image detected; and analysing the control signal in order to detect the possible presence of defects on the portion of side wall.

EP 2322899 describes a method for detecting minute irregularities on the surface of a tyre under inspection. A surface in the region of side wall of a tyre is illuminated by a red light emitted by first illumination means arranged in the direction of 45 degrees with respect to the line normal to the surface. At the same time, the surface is illuminated by a blue light coming from second illumination means arranged in a direction of −45 degrees with respect to the normal line. The illuminated surface is captured by a linear camera from the direction of the normal line. The surface irregularity formed on the surface of the tyre is detected based on the waveforms of luminance distribution.

US 2011/018999 shows a device for evaluating the appearance of the surface of a tyre comprising a linear colour camera including means for separating the beam of light reflected by the surface of said tyre and entering into the camera into at least two primary colours (R, G, B) of certain wavelengths, so as to direct the beam of light to as many sensors capable of obtaining a base image in grayscale for each of the primary colours, a number of illumination means equal to the number of primary colours, said illumination means being oriented so as to illuminate the surface to be evaluated at different angles, characterised in that each illumination means emits a coloured light (R, G, B) different from that emitted by the other illumination means, the wavelength of which substantially corresponds to the wavelength of one of the primary colours selected by the camera.

In the field of the checking of tyres, the Applicant has set itself the problem of analysing the surface, inner and/or outer, of the tyre, through optical image acquisition, for example digital, thereof and their subsequent processing, for example in order to detect the possible presence of visible defects on the surface, minimising the checking by human operators. The defects sought can for example be irregularities on the surface of a tyre (unvulcanised compound, alterations in shape, etc.), structural unevenness, cuts, presence of foreign bodies on the surface, etc.

The Applicant has observed that in order for the check to be able to be used "on line" inside a tyre production plant, it is necessary for the check itself to be carried out in short time periods and with low costs.

Therefore, the method for checking the tyre through acquisition and analysis of images thereof to highlight possible defects thereof preferably takes a time period that is kept within the aforementioned limited "cycle time" period and at the same time ensures an accurate verification of the presence of defects in the tyre itself, at reasonably low cost.

The Applicant has observed that although the above documents in some cases effectively describe devices that can be useful for detecting specific defects in a tyre, in order to detect a plurality of defects a different device would have to be used for each specific defect having specific characteristics for identifying the specific defect. The Applicant has in fact further observed through an analysis of the devices of the type illustrated in WO 2015/004587, EP 2322899 and US 2011/018999 that a specific type of illumination coupled with a camera or different sensor is preferred for the correct detection of a specific defect or of a (limited) plurality of specific defects among the various defects that can occur in a tyre. The Applicant has indeed understood that the use of the same device with the same illumination and camera for the analysis of the entire tyre would lead to the lack of detection, or very difficult detection, through image processing, of some defects and in particular of some two-dimensional defects, i.e. that do not involve an alteration of the height of the surface, like for example the cuts at matching edges.

However, the provision of a large number of different devices each with different characteristics to identify different defects increases the complexity of the tyre production line in the part dedicated to checking them and the costs thereof. Moreover, the provision of distinct devices requires continuous movement thereof towards the tyre when in analysis step and away from it when a different device is in analysis step. This increases the cycle time since the so-called "idle time" in which the translation of the unused devices takes place are substantial, even if necessary to avoid collisions or interference between distinct devices.

The Applicant has therefore set itself the problem of devising a method and an apparatus for checking tyres capable of acquiring images of the surface of a tyre, in particular for detecting more than one type of defect on the surface thereof, which are suitable for application on line inside a tyre production line of a production plant, in other words suitable for being used to obtain reduced operating times and costs, and capable of providing reliable results.

The Applicant has realised that having a detection system with at least two light sources makes it possible to vary the illumination of a portion of the surface of the tyre according to the type of defect wished to be identified and to adapt the acquisition of images both in diffused light and in grazing light particularly useful for the purposes of the aforementioned check of the tyre according to whether or not further devices are used, such as a thrusting element for the deformation of the tyre itself.

More precisely, the Applicant has finally found that a method and an apparatus providing for a first illumination step and a second illumination step of a first surface portion and of a second surface portion of the tyre, respectively, surface portions that can generally have different defects, with consequent acquisition of a first image and of a second image, through the same device coupled, or not, with a thrusting system, allows the checking of the tyre to be made fast. Advantageously, the first illumination step is carried out at the same time as a deformation of the illuminated portion of the surface or at least part thereof, using an illumination coming from a first light source, whereas the second illumination is carried out without compression. This different illumination and acquisition of images is carried out in the invention by the same detection system and by at least two light sources.

In accordance with a first aspect, the invention concerns a method for checking tyres.

Preferably, it is foreseen to provide a tyre to be checked.

Preferably, it is foreseen to associate a first light source and a second light source able to be activated independently with a camera.

Preferably, it is foreseen to apply a first force against a first surface portion of said tyre so as to generate a deformed surface portion.

Preferably, it is foreseen to illuminate said deformed surface portion of said tyre with a first light radiation emitted by said first light source.

Preferably, it is foreseen to keep said second light source inactive during said deformation.

Preferably, it is foreseen to acquire a first image of said deformed surface portion illuminated by said first light radiation through said camera.

Preferably, it is foreseen to remove said first force from said first surface portion of said tyre.

Preferably, it is foreseen to select a second surface portion at least partially distinct from said first surface portion of said tyre.

Preferably, it is foreseen to illuminate said second undeformed surface portion of said tyre with a second light radiation emitted by said second light source.

Preferably, it is foreseen to acquire a second image of said second undeformed surface portion illuminated by said second light radiation through said camera.

Preferably, it is foreseen to process said first image and said second image, so as to detect possible defects in said first surface portion and in said second surface portion of said tyre.

In accordance with a second aspect, the invention relates to an apparatus for checking a tyre.

Preferably, a support plane is provided configured to receive a tyre.

Preferably, a deformation element is provided configured to apply a first force to a first surface portion of said tyre so as to generate a first deformed surface portion.

Preferably, a positioning actuator is provided operatively associated with the deformation element and configured to move said deformation element towards and away from said surface of said tyre.

Preferably, a device including a camera is provided.

Preferably, the device includes a first light source.

Preferably, the device includes a second light source.

Preferably, a processing unit is provided programmed to activate said positioning actuator so as to move said deformation element towards said tyre to apply a force to a first surface portion of said tyre so as to generate a first deformed surface portion.

Preferably a processing unit is provided programmed to activate said positioning actuator so as to remove said first force from said first surface portion of said tyre.

Preferably, the apparatus comprises a drive and control unit programmed to actuate said first light source so as to illuminate said first deformed surface portion of said tyre, keeping said second light source inactive during said deformation of said first surface portion.

Preferably, the drive and control unit is programmed to control said camera so as to acquire a first image of said first deformed surface portion illuminated by said first light source.

Preferably, the drive and control unit is programmed to actuate said second light source so as to illuminate a second undeformed surface portion of said tyre at least partially distinct from said first surface portion.

Preferably, the drive and control unit is programmed to control said camera so as to acquire a second image of said second undeformed surface portion illuminated by said second light radiation.

Preferably, said processing unit is programmed to process said first image and said second image, so as to detect possible defects in said first surface portion and in said second surface portion of said tyre.

The Applicant considers that providing a method and an apparatus in which a single device is capable of carrying out different types of analysis for detecting different types of defects makes the more general method for checking a tyre faster and more reliable, with low costs. The Applicant has indeed studied and provided a method and an apparatus in which it is possible to minimise the number of devices necessary to carry out many distinct measurements using a first optimised source for the illumination of defects visible through compression in a first portion of tyre in combination with a second source for illuminating a second portion of tyre in an optimised manner to detect another type of defect.

The present invention, in at least one of the aforementioned aspects, can also have one or more of the preferred characteristics described hereinafter.

Preferably, said first light source is suitable for emitting diffused light radiation and said second light source is suitable for emitting grazing light radiation.

Preferably, said second light source comprises a first sub-light source emitting a first sub-light radiation and a second sub-light source emitting a second sub-light radiation, in which for each point of said second surface said first sub-light radiation and said second sub-light radiation come, respectively, from two opposite half-spaces with respect to an optical plane of said camera.

Advantageously, this particular arrangement of the light sources makes it possible both to come particularly close to the tyre when the compression thereof is carried out to detect a first type of defects in the first surface portion, and to illuminate correctly and with the necessary power to identify defects that could be present in the second surface portion.

More preferably, it is foreseen to arrange said first sub-light source and said second sub-light source symmetrically with respect to said first light source.

A symmetry in the sources, in this case of the second source that comprises a first sub-source and a second sub-source, which are arranged at the two sides of the optical plane of the detection system, allows easier comparison of images detected by the camera while the second surface portion is illuminated with the first sub-light radiation or with the second sub-light radiation. These illuminations are different for their different specular provenance.

Preferably, illuminating with a first light radiation comprises illuminating said first surface portion or said second surface portion with a first diffused light radiation.

Preferably, illuminating with a second light radiation comprises illuminating said second surface portion with a first grazing sub-light radiation or a second grazing sub-light radiation.

The first light source preferably emits a radiation on the first surface portion or on the second surface portion that, at the level of the first surface portion or second surface portion, is diffused, whereas the first sub-light source or second sub-light source emits a radiation on the second surface portion that, at the level of the second surface portion is grazing. The first surface portion, deformed by the compression, preferably only need diffused light to identify defects, whereas the second surface portion preferably needs an illumination with grazing light and more preferably with two different types of radiation, grazing and diffused, so as to obtain the acquisition of at least two images for the same second surface portion, each with different illumination, which can be compared with each other to identify the defects on the second surface portion.

Preferably, for each point of said second surface portion at least 90% of the respective total light power of said first sub-light radiation and second sub-light radiation incident in the point comes, respectively, from said two opposite half-spaces defined by said optical plane.

More preferably, for each point of said second surface portion the entire respective total light power of said first sub-light radiation and second sub-light radiation incident in the point comes, respectively, from said two opposite half-spaces. In this way, the contrast between the two illuminations is accentuated.

Preferably, at least 75% of the respective total light power of said second light radiation incident on each point of said second surface portion forms a first angle of incidence of size less than or equal to 55° with a plane tangent to the surface of said tyre in said each point.

Preferably, at least 75%, more preferably at least 90%, of the respective total light power of said first sub-light radiation and second sub-light radiation incident on each point of said second surface portion forms a first angle of incidence of size less than or equal to 55°, more preferably less than or equal to 50° with a plane tangent to the surface of said tyre in said each point. In this way, the grazing effect of the light is accentuated.

Preferably, at least 75%, more preferably at least 90%, of the respective total light power of said first sub-light radiation and second sub-light radiation incident on each point of said second surface portion forms a first angle of incidence of size greater than or equal to 10°, more preferably greater than or equal to 20°, even more preferably greater than or equal to 30° with a plane tangent to the surface of said tyre in said each point. In this way, the illumination is possible also with light sources arranged in close proximity to the surface of the tyre.

Preferably at least 75%, more preferably at least 90%, of the respective total light power of said first sub-light radiation and second sub-light radiation incident on each point of said second surface portion forms a second angle of incidence less than or equal to 45°, more preferably less than or equal to 30°, in absolute value, with a reference plane perpendicular to said optical plane in said each point and passing through the normal to the surface in said each point.

In this way, the difference in illumination between the first light radiation and the second light radiation is accentuated.

Preferably, providing a tyre includes arranging said tyre on a support plane with axial mid-plane substantially parallel to the support plane, defining a resting side portion and a free side portion arranged at a certain height with respect to said support plane.

Preferably, applying a first force includes applying said first force against a surface portion of said free side surface.

In order to obtain correct support of the tyre during inspection, it is preferable for it to be rested on a plane so that a rotation axis of the tyre is substantially perpendicular to the support plane. In this way, the tyre is particularly stable and easy inspection of at least half of said tyre is allowed.

Preferably, said first force includes a component in the direction of a rotation axis of said tyre. The tyre is thus "compressed" along its rotation axis so as to highlight defects, like for example cuts, which may be formed along a sidewall or a shoulder thereof.

More preferably, said component of said first force is in a direction towards said mid-plane. Advantageously, the tyre is compressed from the outside towards the inside, i.e. it is compressed by applying a force in an outer surface portion thereof facing towards the inside of the tyre.

Preferably, it is foreseen to bring said first light source towards said first deformed surface portion at a distance comprised between about 25 mm and about 55 mm, more preferably between about 35 mm and about 45 mm. The defects searched for can for example be irregularities on the surface of a tyre (unvulcanised compound, alterations in shape, etc.), structural unevenness, presence of foreign bodies on the surface. Among structural unevenness defects, so-called "carcass creep" are particularly critical, which are rare but potentially very dangerous defects, generated in the interface region between two portions of the tyre having different chemical-physical characteristics, like for example different compounds.

Such defects are in the form of small cuts, typically extending longitudinally, i.e. they follow the circular extension of the tyre, characterised by perfectly matching edges—between which there is no removal or lack of material, this being a characteristic that makes them particularly difficult to identify. The compound running can involve areas of the tyre arranged both inside and outside of the tyre itself, for example close to the inner surface, below the liner layer whereas on the outside a non-adhesion of two adjacent compounds can generate cuts typically in the buttress or sidewall area.

By suitably deforming a first portion of side wall of a tyre to be checked it is possible to decrease the outer radius of curvature of a deformed surface portion of the tyre, thus highlighting possible defects, in particular compound running and other cuts or holes, since the accentuation of the normal external convexity tends to 'open' the edges or perimeters of such defects, making them easier to identify in the subsequent image processing.

The images detected of this adequately compressed first surface portion thus have a high quality and/or contain information in number and quality such as to allow a subsequent automatic processing of the latter in order to detect possible defects existing, making the algorithms for automatically detecting defects used for this purpose highly effective.

This type of defect, in order to be properly identified, requires an illumination of relative high power and close to the deformed portion of tyre, i.e. positioning of the device very close to the thrusting element, otherwise the cut opened by the thrusting element "closes" as soon as a distance is reached from the area in which the deformation takes place.

Preferably, it is foreseen to bring said first light source towards said second surface portion at a distance comprised between about 25 mm and about 55 mm, more preferably between about 35 mm and about 45 mm. This range of distances has been found to be optimal for correct visualisation of the defects: the distance at which the first light source is positioned is an optimal compromise between the minimum distance so as not to hit the tyre or an element that applies a compression force on it.

Preferably, it is foreseen to apply a second force against a third surface portion of said tyre so as to generate a second deformed surface portion, said third surface portion being at least partially distinct from said first surface portion and from said second surface portion of said tyre.

Preferably, it is foreseen to illuminate said second deformed surface portion of said tyre with said first light radiation emitted by said first light source.

Even more preferably, it is foreseen to acquire a third image of said further deformed surface portion illuminated by said first light radiation through a detection system. Advantageously, more than one surface portion of tyre is checked through the device by applying a force in different portions of the tyre. In this way, defects in various positions of the surface can be detected.

Preferably, said first surface portion or said third surface portion belongs to said free side surface. The tyre is advantageously examined in the free side surface, i.e. the surface not in contact with a support. Preferably, in order to examine the side surface in contact with the tyre substantially symmetrical to the free side surface, the tyre is rotated by 180° perpendicularly to its rotation axis so that the side surface previously in contact with the support becomes the free side surface and can be examined.

Preferably, illuminating said second surface portion includes illuminating said second surface portion with said first light radiation.

Preferably, illuminating said second surface portion includes illuminating said second surface portion with said second light radiation at a different time with respect to the time at which said first light radiation illuminates said second surface portion.

The type of defects searched for in the second surface portion of the tyre is identified preferably by comparing images acquired through the detection system in different illumination conditions, like the first light radiation and the second light radiation, so that the defect is detectable for example through a "subtraction" of the characteristics detectable in one image from the other.

Preferably, illuminating said third surface portion with a first light radiation comprises illuminating said third surface portion with a first diffused light radiation. Advantageously, the type of illumination of the third portion is substantially analogous to the type of illumination of the first surface portion.

Preferably, illuminating said second surface portion includes illuminating said second surface portion with said first light radiation.

Preferably, illuminating said second surface portion includes illuminating said second surface portion with said first sub-light radiation at a different time with respect to the time at which said first light radiation illuminates said second surface portion;

Even more preferably, illuminating said second surface portion includes illuminating said second surface portion with said second sub-light radiation at a different time with respect to the time at which said first light radiation illuminates said second surface portion and said first sub-light radiation illuminates said second surface portion.

The three distinct images acquired to be processed are each with a different type of illumination. This allows a comparison of three distinct images and their processing with suitable algorithms in order to highlight the possible defects in the second surface portion.

More preferably, acquiring said second image includes acquiring a first image to be processed when said second portion is illuminated by said first light radiation.

Even more preferably, acquiring said second image includes acquiring a second image to be processed when said second portion is illuminated by said first sub-light radiation.

Even more preferably, acquiring said second image includes acquiring a third image to be processed when said second portion is illuminated by said second sub-light radiation.

The three images to be processed, two preferably in grazing light and one in diffused light, are thus advantageously processed to identify defects.

Even more preferably, said first image to be processed, second image to be processed or third image to be processed are made up of a respective plurality of first linear images, second linear images or third linear images of a succession of linear surface portions, contiguous to one another or partially overlapping, said first linear images, second linear images or third linear images being acquired on each linear portion of said succession of linear portions illuminated, respectively, by said first light radiation, first sub-light radiation and second sub-light radiation in alternate sequence.

Advantageously, said first image, said second image, said third image or said images to be processed are digital images. More preferably they are images formed from pixel matrices.

Preferably, said first image or said third image is made up of a respective plurality of fourth linear images of a succession of linear surface portions, contiguous to one another or partially overlapping, said fourth linear images being acquired on each linear portion of said succession of linear portions illuminated, respectively, by said first light radiation.

A type of detection system for acquiring images is for example a linear camera defining a lens line, intersection of the lens plane on a focal plane in which or close to which the first surface portion or the second surface portion or the third surface portion is preferably arranged when illuminated. The linear portions are therefore preferably surface portions able to be obtained close to said lens line in temporal succession. For example, such a succession of linear portions can be obtained by rotating the tyre about a rotation axis thereof, or by rotating the detection system and the light sources about the tyre. Preferably, at least one complete rotation of 360° is completed. More preferably, a rotation of more than 360° is carried out to have correct overlapping between the initial and end part (which must match) of the tyre where the images start and finish being taken, respectively.

Preferably, it is foreseen to rotate said tyre about its rotation axis; and to illuminate said tyre in a plurality of angular positions of said tyre so as to obtain a plurality of first images or of second images or of third images at different angular positions, a first image, or a second image, or a third image for each angular position of said tyre.

Advantageously, the tyre is rotated, instead of the detection system, since the first operation is simpler: the rotation of the detection system could lead to it being damaged or inaccurate acquisition of the images due to vibrations induced by the continuous movement.

Preferably, said first surface portion or said third surface portion is an outer surface portion of a sidewall or of a shoulder of said tyre.

Preferably, said second surface portion is a surface portion of a bead of said tyre.

Preferably, the first type of defects mentioned, in which preferably a strong illumination and a compression of the surface portion under examination are necessary, is a defect that can be found at the sidewall or shoulder of the tyre. The second type of defect, requiring a plurality of different illuminations, is most frequent at the level of the bead of the tyre.

Preferably, applying a first force or a second force includes applying a constant pressure to said first deformed surface or to said second deformed surface of said tyre during said rotation.

Even more preferably, a value of said constant pressure depends on a type of said tyre to be checked.

Preferably, applying a first force or a second force against a first surface portion of said tyre or against a third surface portion of said tyre so as to generate a first deformed surface portion or a second deformed surface portion includes keeping said first deformed portion or second deformed portion at a predetermined height with respect to a support of said tyre.

A deformation can be applied either at constant force or at constant height. Both can be used and the most advantageous is selected according to the specific application or the type of tyre to be checked.

More preferably, said height depends on the model of tyre to be checked.

In fact, not all tyres are the same size or have the same rigidity and therefore the height at which to position the deformed surface of the tyre is preferably selected based on the characteristics of the tyre itself.

Preferably, it is foreseen, before illuminating said second surface portion, to move said second light source from a first inactive configuration where it is controlled not to emit light radiation and in which the distance of said second source from a focal plane of said camera is greater than the distance of said first source from said focal plane to an active configuration in which it is adapted to emit a second light radiation and in which the distance of said second source from said focal plane is equal to or less than the distance of said first source from said focal plane.

In this way, two illuminations can be obtained by moving the first sub-light source and the second sub-light source according to whether one or both are necessary. When in inactive configuration, the device is particularly compact and adapted for going substantially close to the first or third surface portion of the tyre, which is deformed. In the second configuration, with the first sub-source and the second sub-source "open", it is possible to obtain a plurality of different illuminations of the second surface portion through the different sources. In the second configuration, in fact, the compactness is less necessary since neither the compression means nor the consequent deformed surface are present, both no longer necessary for detecting the defect sought, for example a cut in the bead area.

Preferably, a robotic arm is provided coupled with one end to said device. Through a robotic arm, the device for the illumination of surface portions of the tyre is easily moved so as to reach the position of the portion to be examined.

Preferably, the processing unit is programmed to move said robotic arm towards said first deformed surface so that said first light source of said device is brought to a distance comprised between about 25 mm and about 55 mm from said deformed surface, more preferably between about 35 mm and about 45 mm.

Preferably, said deformation element includes a thrusting roller.

More preferably, the thrusting roller is mounted so as to be able to rotate freely about its own axis. Advantageously, the compression takes place through the roller resting against a surface portion of tyre. The roller, being able to rotate, keeps the portion compressed for a rotation of the tyre about its rotation axis, so that the same surface can be checked in any angular position.

Preferably, the tyre is set in rotation and the position of the roller remains the same, rotating about its axis due to the rotation of the surface of the tyre with which it is in contact.

More preferably, the axis of the thrusting roller lies on a plane passing through a rotation axis of the tyre and through the radial direction of the deformed surface portion. In this way, an optimal compression of the surface of the tyre is carried out.

Preferably, said rotation axis of said thrusting roller can be positioned at a predetermined angle with a rotation axis of said tyre. In this way, it is possible to "follow" the geometric shape of the surface of the tyre in an optimal manner, suitably inclining the rotation axis of the roller, so as to apply a correct pressure that is not modified by the geometric shape of the tyre.

Preferably, the thrusting roller can be positioned in two distinct positions. In the first, the rotation axis of the roller is substantially perpendicular to the rotation axis of the tyre. In the second, the rotation axis of the roller and the rotation axis of the tyre form an angle of about 120°.

Preferably, said roller includes a portion with increased section at a central portion along said rotation axis and a portion with reduced section at an end thereof along said rotation axis. The central portion with increased section is preferably positioned at the shoulder or sidewall area where it is wished to look for defects. However, a large central portion can in certain situations create vibrations passing over the blocks of the tyre. For this reason, a tapering of the axial ends of the roller itself is preferable, so that the area of the surface engaged by the compression of the roller is limited and adjustable.

Further characteristics and advantages will become clearer from the detailed description of some example, but not exclusive, embodiments of a method and a device for checking tyres, in accordance with the present invention. Such a description will be outlined hereinafter with reference to the attached figures, provided only for indicating and therefore not limiting purposes, in which.

Figure 2:
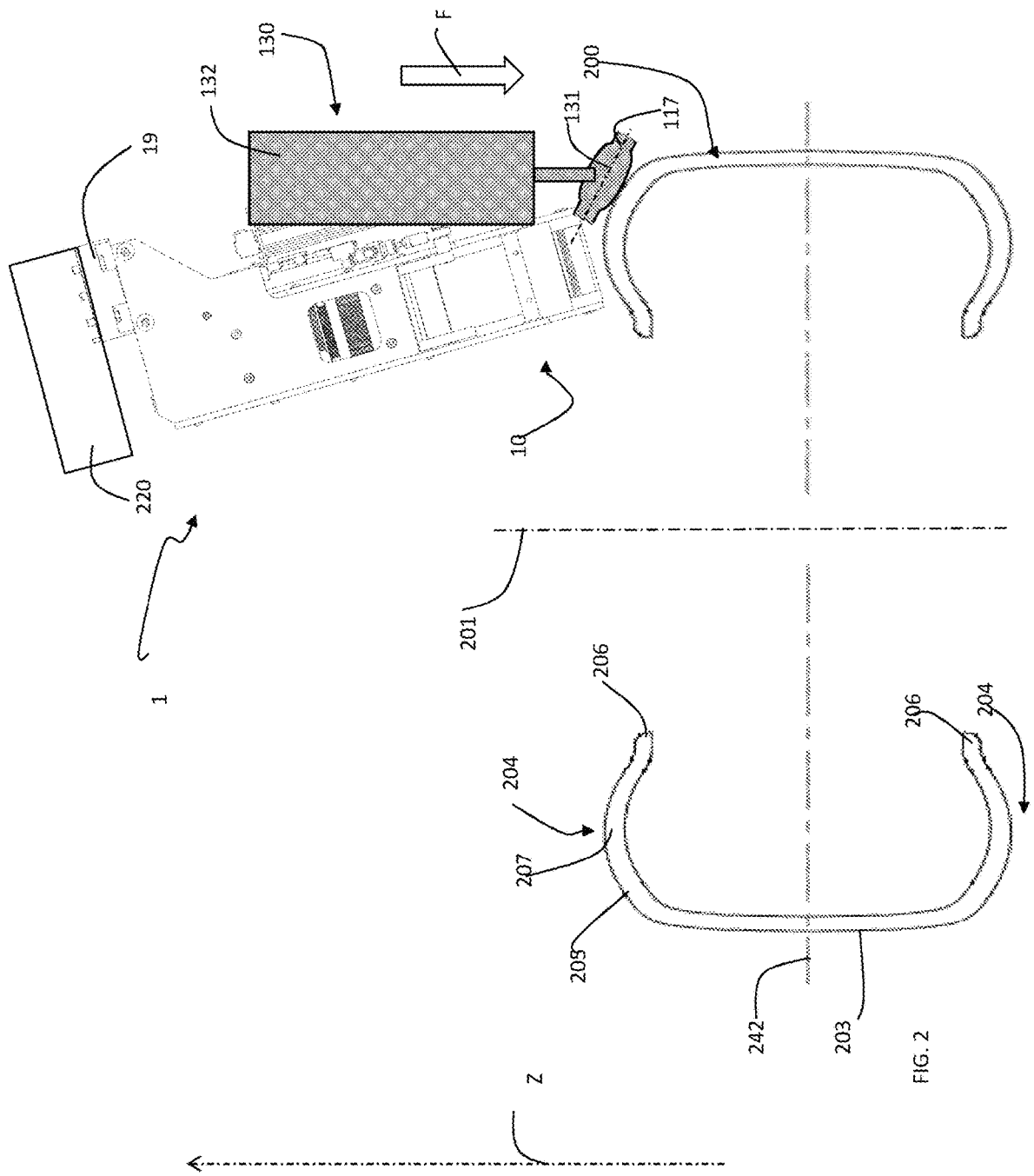
FIG. 2 shows a partial and schematic perspective view of the apparatus for checking tyres in accordance with the present invention of FIG. 1 in an operative step.
Figure 3:
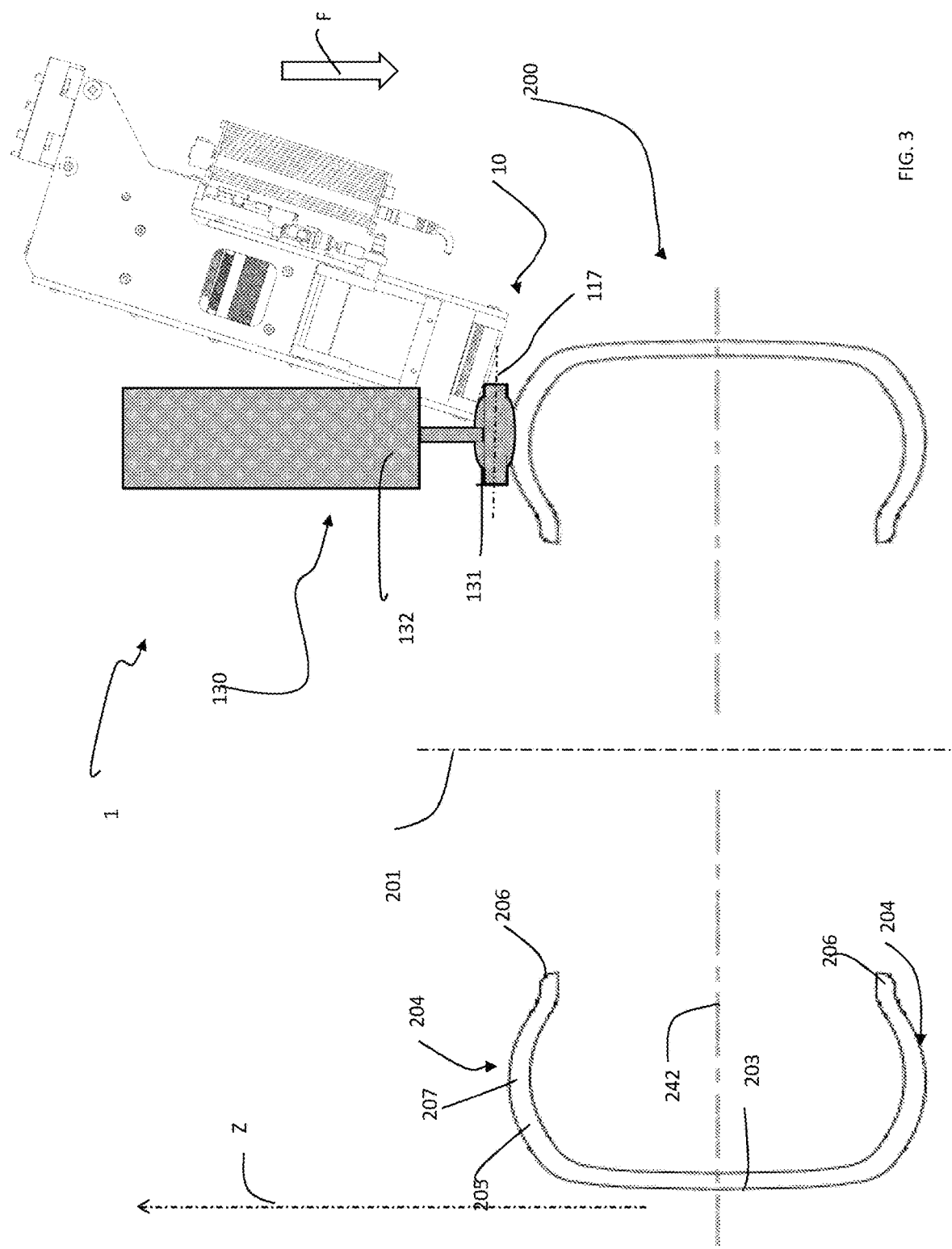
FIG. 3 shows the apparatus of FIG. 2 in a distinct operative step.
Figure 4A:
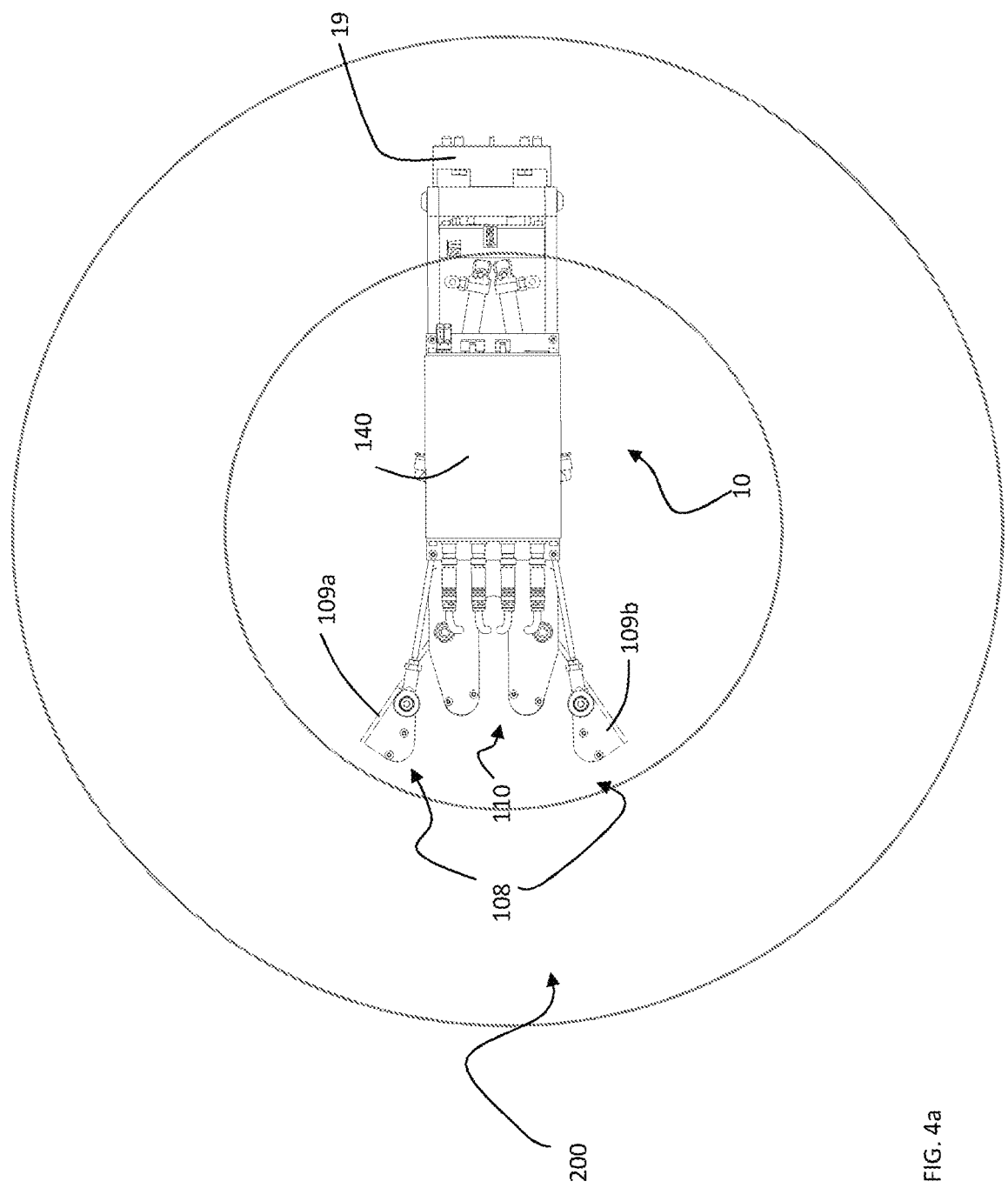
Figure 8:
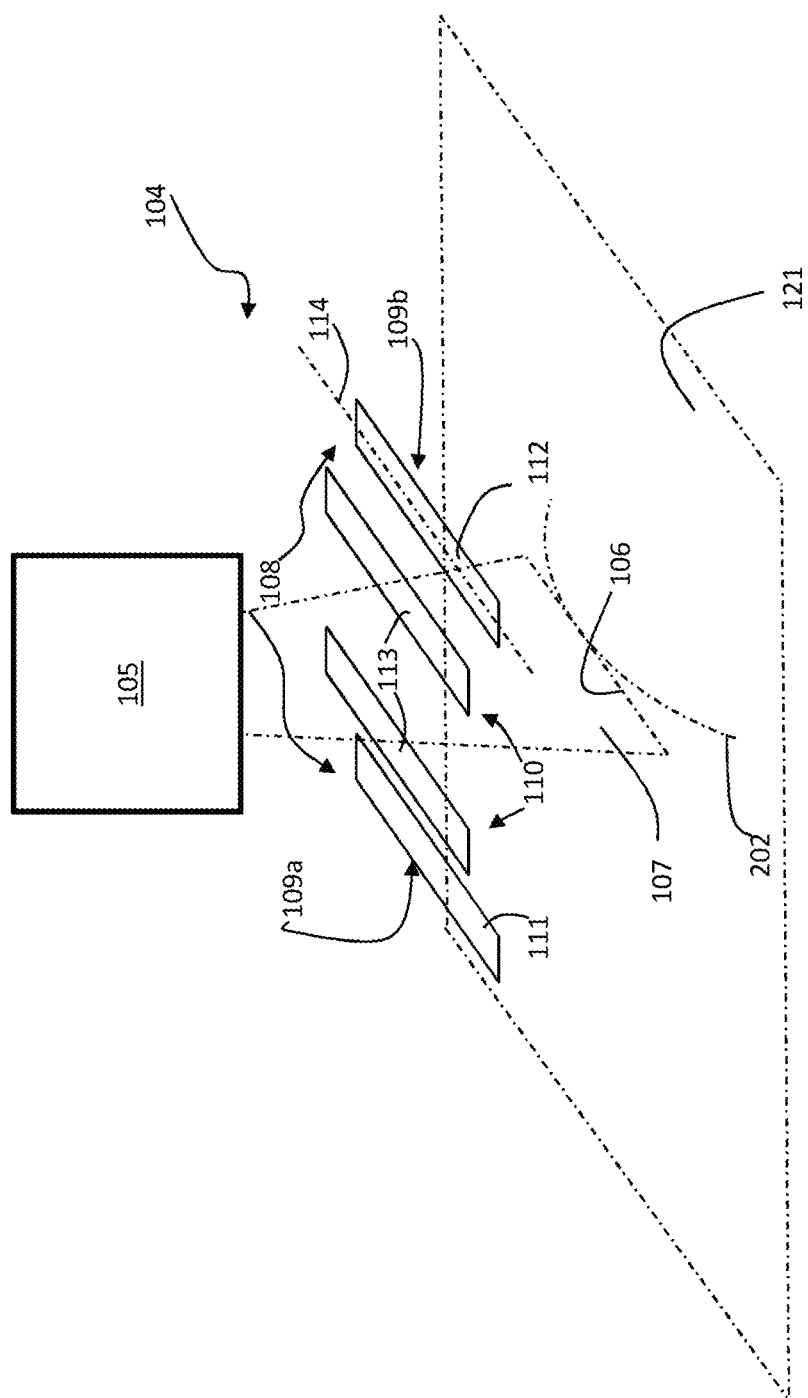
Figure 9B:
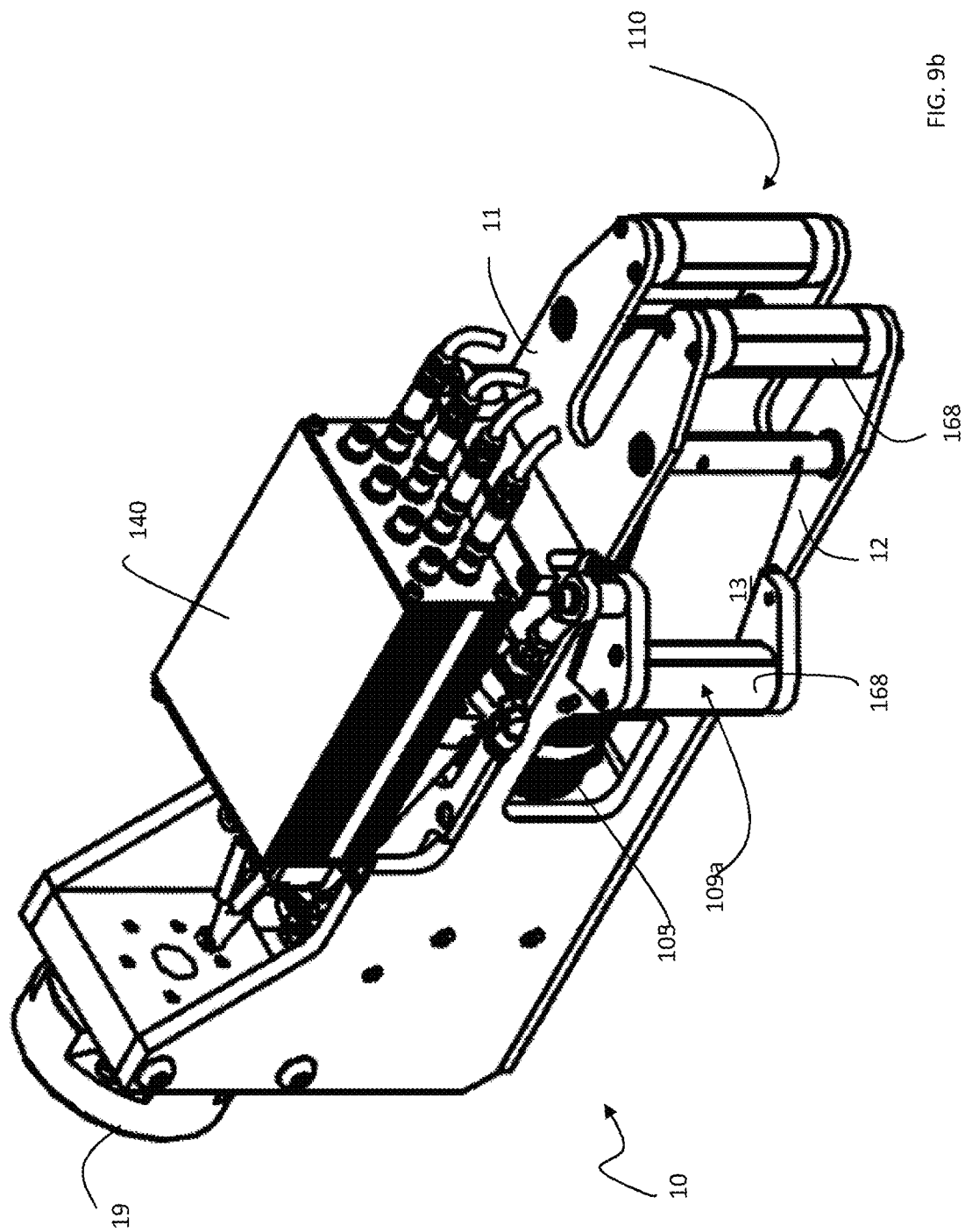

FIG. 3*a* shows a detail of the apparatus of FIG. 3 in enlarged scale;

FIG. 4 shows the apparatus of FIGS. 2-3 in a further operative step;

FIG. 4a shows a view from above of the apparatus in the operative configuration of FIG. 4;

FIG. 5 shows a partial and schematic side view of a detail of the apparatus of FIG. 2 or 3;

FIG. 6 shows a partial and schematic side view of a detail of the apparatus of FIG. 4;

FIG. 7 shows a schematic section side view of a detail of FIG. 5 or 6;

FIG. 8 shows a partial and schematic perspective view of a detail of the apparatus of FIG. 2 or 3;

FIG. 9a shows a perspective view of a device for checking tyres in an operative configuration in accordance with the present invention;

FIG. 9b shows a perspective view of the device for checking tyres of FIG. 9a in a different operative configuration;

FIG. 10 shows a view from above of the device of FIG. 9a;

FIG. 11 shows a front view of the device of FIG. 9a;

FIG. 12 shows a view from above of the device of FIG. 9b; and

FIG. 13 shows a front view of the device of FIG. 9b.

Figure 1:
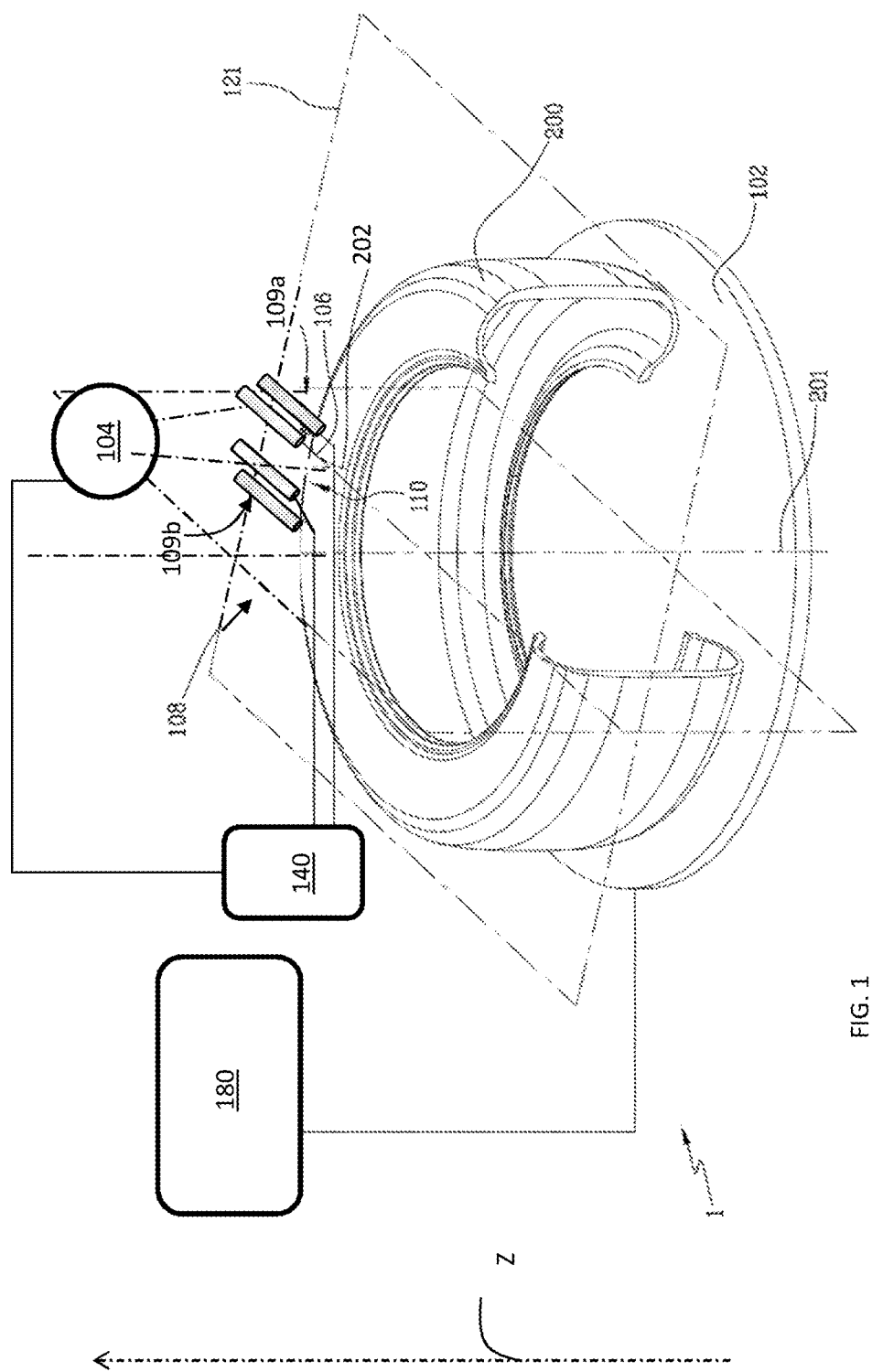
FIG. 1 shows a partial and schematic perspective view, partially in section and partially in terms of functional blocks, of an apparatus for checking tyres in a tyre production line.

An apparatus for checking tyres in a tyre production line according to the present invention is globally indicated with 1 and depicted in FIG. 1. In general, the same reference numeral will be used for possible variant embodiments of similar elements.

The apparatus 1 comprises a support 102 (only visible in FIG. 1) adapted for supporting a tyre 200 on a sidewall and for rotating it about its rotation axis 201, typically arranged according to the vertical. The support 102 is typically actuated by a moving member not described and illustrated any further, since it can as an example be of the known type. The support for the tyre can possibly be configured to lock it, for example the respective resting bead. The tyre 200 rested in the support therefore defines a free side surface or free sidewall, representing that surface portion not resting on the support and facing, in a system of coordinate axes with an axis Z perpendicular to the plane of the support, upwards.

The tyre 200 has a substantially toroidal structure about the rotation axis 201, and has an axial mid-plane 242 (represented in section by a broken line in FIGS. 2, 3 and 4) perpendicular to the rotation axis 201. The tyre is made up of a crown 203 and side walls 204. In turn, the latter are each made up of a shoulder area 205, a bead area 206 and a radially central or sidewall area 207 interposed between shoulder and bead.

Typically, as represented now in FIGS. 2 and 3, the apparatus 1 comprises a robotic arm 220 on which a device 10 is mounted, and in particular the device 10 comprises an attachment member 19 for coupling with an end of the robotic arm 220. The robotic arm 220 represented in a very schematic manner in FIG. 2, is preferably an anthropomorphic robotic arm. Even more preferably, it is an anthropomorphic robotic arm with at least 5 axes.

Preferably, the apparatus 1 also includes a deformation element 130. The deformation element 130 is configured to apply, through physical contact, a compression force on an outer contact surface belonging to a portion of a side wall of the tyre 200 in order to elastically deform a portion of side wall, preferably of the free side surface. In a preferred configuration, shown as an example in FIGS. 2 and 3, the compression force (indicated by the vertical arrow F in FIGS. 2 and 3) is directed like a rotation axis 201 of the tyre 200. However, according to the Applicant the present invention includes the cases in which the compression force has at least one component parallel to the rotation axis 201.

Preferably, the deformation element 130 comprises a compression member 131 and a positioning actuator 132 adapted for moving the compression member along the direction of the compression force. As an example, the positioning actuator 132 can be a pneumatic cylinder. Therefore, the compression member can be brought into contact with or away from the tyre 200. Preferably, the compression member 131 comprises a thrusting roller.

Preferably, the thrusting roller is rotatable about its rotation axis, indicated with 117 in the figures. The axis 117 of the thrusting roller always sits on a plane passing through the axis of the tyre and through the radial direction of the portion of side wall subjected to deformation (for example the plane of FIGS. 2 and 3). Preferably, the axis 117 of the thrusting roller, in the absence of forces, in other words in rest position, is perpendicular to the axis of the tyre. The axis of the roller, in operation, can diverge from such a perpendicular condition with the axis of the tyre (as shown for example in FIG. 2) for example within the range +30° from the perpendicular condition.

Furthermore, the thrusting roller, visible in detail in FIG. 3a, comprises a section, taken in a plane perpendicular to the rotation axis 117, that is substantially circular. A diameter of the section is preferably variable, from a minimum diameter present at a first end 118a and a second axially opposite end 118b of said roller along the rotation axis 117, to a maximum diameter present in a central area of the roller.

Preferably, the deformation element 130 comprises a radial movement member (not shown, for example a further electric motor and a system of guides and sliding blocks to guide the radial movement) adapted for moving the compression member 131 and the positioning actuator 132 as a unit along the radial direction of the tyre. Therefore, the deformation element 130 can be taken away from the tyre when not in use.

Preferably, the deformation element 130 is adapted for elastically deforming a portion of a side wall of the tyre 200, applying a compression force on an outer contact surface belonging to the portion of side wall, pressing the aforementioned thrusting roller on the outer contact surface. The force applied or the movement imposed on the outer contact surface along a rotation axis of the tyre is predetermined and depends on the type of tyre to be checked. The tyres 200 can have a different elasticity and deformability according to the type and model, and therefore the force applied or the deformation imposed by the deformation element 130 is preferably dependent on the type of tyre 200 to be checked.

The device 10, with initial reference to FIGS. 5-8, comprises a detection system 104 including a camera 105. Preferably, the camera 105 is a linear camera having a lens line 106 lying on an optical plane 107 passing through the camera itself (visible in FIGS. 5, 6 and 8). The present invention also considers the alternative case in which the camera 105 is of a different type, like for example a matrix camera. In this case, the surface portion illuminated and acquired is also of the matrix type. Moreover, the camera 105 defines a focal plane 121 in which a portion to be illuminated of tyre surface is focused upon. Preferably, the optical plane 107 and the focal plane 121 are perpendicular to each other (visible in FIGS. 5, 6 and 8).

The device 10 also comprises a first light source 110 and a second light source 108 adapted for emitting, respectively, a first and a second light radiation to illuminate a surface portion 202, preferably linear (visible in FIG. 8), of said tyre 200 coinciding with the lens line 106 (for example when the surface portion is planar) or close to the lens line 106 (due to the curvilinear shape of the surface of the tyre).

The detection system through the camera 105 is adapted for acquiring a respective two-dimensional digital image of the surface portion 202 (linear) illuminated by at least one from the first and the second light radiation.

Preferably, the second light source 108 comprises a first sub-light source 109a and a second sub-light source 109b. Each sub-light source 109a and 109b can comprise one or more source elements. Preferably, each sub-light source 109a and 109b comprises a single respective source element 111 and 112, respectively. The two source elements 111, 112 are positioned symmetrically with respect to the optical plane 107. Preferably, the two source elements 111 and 112 respectively sit on opposite sides with respect to the optical plane and are equidistant from it.

Preferably, the first light source 110 comprises two respective source elements 113 distributed on both sides of the optical plane 107 and symmetrically with respect to such a plane.

Each source element 111, 112, 113 has a respective main direction of extension (indicated as an example with the broken lines 114 in FIG. 8) preferably substantially parallel to the optical plane 107 and thus to the lens line 106.

As an example, the source elements 111, 112, 113 have a dimension along the main direction of extension 114 equal to about 60 mm, and a diameter perpendicular to the aforementioned main direction of extension 114 equal to about 25 mm. Each source element 111, 112, 113, typically comprises a plurality of LED sources 169 arranged aligned along the main direction of extension 114. Preferably, as can be seen in FIG. 7, each source element 111, 112, 113, comprises, positioned above each LED light 169, a converging lens 170, adapted for converging the light beam emitted by the LED light by about 30°. The beam of light emitted by each LED light is therefore preferably restricted within an angle comprised between about 20° and about 40°.

In FIGS. 5, 6 and 8, the elements of the light sources 111, 112, 113 are shown schematically with reference to their respective emitting surface (in the figures as an example semi-circular in shape, however it can be of any shape), which can for example coincide with the transparent protective glass and/or diffusor.

As can be seen from FIGS. 5 and 6, the device, and in particular its light sources, can be moved from a first operative configuration to a second operative configuration and vice-versa.

In the first operative configuration of FIG. 5, preferably the distance $d_1$ of each of the source elements 113 of the first light source 110 from the optical plane 107 is greater than the distance $d_2$, $d_3$ between each source element 111, 112 of said second light source 108 and the optical plane 107.

Advantageously, in the second configuration of FIG. 6, the distance $d_1$ between the first source 110 at the source elements 113 and the focal plane 121 is less than the distance $d_2$ or $d_3$ of the first sub-light source 109a or second sub-light source 109b from the focal plane 121. More preferably $d_1$ is less than both $d_2$ and $d_3$. Even more preferably $d_2=d_3$. Preferably, in both configurations, the two source elements 113 of the first light source 110 are coplanar and define a plane P1 substantially parallel to the focal plane 121, being a distance $d_1$ from it, i.e. the source elements 113 of the first light source are the same distance from the focal plane 121. The plane P1 can be defined as the plane passing through the points of both source elements 113 of the first light source 110 at minimum distance from the focal plane 121 (as represented in FIGS. 5 and 6), or as the plane passing through a middle line of both source elements 113.

Preferably, the sub-light sources 109a and 109b, preferably both in the first and in the second operative configuration, are also coplanar and define a plane P2 substantially parallel to the focal plane 121. Preferably, the distance of this plane P2 from the focal plane 121 is equal to $d_2$ (con $d_2=d_3$). Like for P1, the plane P2 can be defined as the plane passing through the points of both sub-light sources 109a and 109b at minimum distance from the focal plane 121 (as represented in FIGS. 5 and 6), or the plane passing through a middle line of both sub-light sources 109a-109b.

Preferably, in the first and/or in the second configuration, the distance $d_1$ is equal to about 77 mm.

More preferably, in the first configuration, the distance $d_1$-$d_2$=$d_1$-$d_3$ is equal to about 32 mm (77 mm-45 mm).

An embodiment of this device is represented in FIGS. 9a, 9b, and 10 to 13.

Each light source 108, 110 includes a support, preferably made of aluminium, on which the LEDs 169 are fixed. The supports are all indicated with 168 in the attached figures (see FIGS. 9a, 9b and 13). Preferably, the LEDs 169 are fixed to the respective support 168 through a thermo-conductive paste (not visible in the figures). Advantageously, each support 168 also includes, in an outer surface not in contact with the LEDs, a fin arrangement 167 for the dissipation of heat (visible in FIGS. 9a and 13).

The first and the second source element 113 of the first light source 110 are positioned between two plates 11, 12 arranged substantially perpendicular to the main direction of extension 114 of the first light source 110 and substantially parallel to one another. Between the two plates 11, 12, which extend downstream of the first light source in the direction of emission of the light, the linear camera 105 is also positioned.

These two plates 11, 12 are hinged to a third and a fourth plate 13, 14, so that the rotation axis of the third and fourth plate thus defined is substantially parallel to the main direction of the first light source 110 or of the second light source 108. The third plate 13 is firmly connected to the first sub-source 109a of the second light source 108, whereas the fourth plate 14 is firmly connected to the second sub-light source 109b of the second light source 108.

Third and fourth plate 13, 14 are rotationally moved by a first and a second pneumatic piston 15, 16, visible in extended condition in FIGS. 9a and 10. Each piston 15, 16 is connected at one end to the plate to be moved, and at the other end to the first plate 11.

The movement of the plates 13, 14 through the pistons means that the device 10 can be brought into the first operative configuration such as that of FIGS. 9a, 10 and 11 in which the second light source 108, i.e. the sub-sources 109a and 109b, are brought "forwards", i.e. they are further from the camera 105 with respect to the first light source 110 and closer to the tyre surface to be illuminated, i.e. closer to the focal plane 121 with respect to the first light source 110; or in the second configuration, such as that represented in FIG. 9b, in which the second light source 108 is positioned further away with respect to the focal plane 121, the first sub-source 109a and the second sub-source 109b are substantially bent parallel to the optical plane 107 to minimise a bulk given by the device 10 in a direction perpendicular to the optical plane 107.

Preferably, both in the first operative configuration and in the second operative configuration, as can be seen more clearly from the respective FIGS. 11 and 13, the source elements of the first light source 110 and of the second light source 108 are arranged so that for their entire extension in a view perpendicular to the optical plane 107 they lay between two planes perpendicular to the lens line. In other words, all of the first and second ends of the sources 108 and 110 with respect to the main direction of extension 114 lay on a respective plane perpendicular to the lens line.

Preferably, the device 10 comprises a drive and control unit 140 configured to selectively activate one or more of said first light source 110, and said second light source 108 and activate the linear camera 105 to acquire a respective two-dimensional digital image (in colour or monochromatic) of the linear surface portion, preferably in synchrony with the activation of one or more of said first light source 110 and second light source 108.

Preferably, the drive and control unit 140 is fixed to said support plate 11 of the first light source 110 and of the camera 105 so as to send signals relative to the control of the light sources 108, 110, without waiting times. Preferably, moreover, the drive and control unit 140 is adapted for controlling the second light source 108 to not emit any radiation when in the second configuration and to emit light radiation when in the first configuration.

For greater heat dissipation, moreover, the unit 140 also comprises a fin arrangement 166 (visible in FIG. 9a).

The processing unit 180, on the other hand, (illustrated in FIG. 1) is preferably adapted for controlling the pistons 15, 16 so as to move the sub-light sources 109a and 109b of the second light source 108. Preferably, the processing unit 180 is also adapted for controlling the deformation element 130 and the robotic arm 220 so as to bring the deformation element 130 towards or away from the tyre 200 to deform, or not, a surface portion, while the robotic arm 220 carries the device 10 to a predetermined distance from the surface of the tyre to be illuminated and to be checked.

Preferably, the second light source 108 is suitable for illuminating the lens line 106 with grazing light. Preferably, the first light source 110 is adapted for illuminating the lens line 106 with diffused light.

Preferably, the apparatus 1 is made to operate according to the method of the invention.

A first surface portion to be checked (always indicated with 202) is selected in the outer surface of the tyre 200. Preferably, but not exclusively, this portion belongs to the shoulder or to the sidewall of the tyre 200. The processing unit 180 takes the device 10 into the second configuration of FIGS. 9b, 12, 13 and 6, whereas the drive and control unit 140 controls the second light source 108 to not emit any radiation. The device 10 is particularly compact for the positioning of the sub-light sources 109a and 109b substantially parallel to the optical plane 107.

The processing unit 180 controls the deformation element 130 to make contact with the tyre, preferably at its side wall 204, so as to apply a force against it and deform a first surface portion thereof including the selected first portion, as can be seen in FIG. 2. Preferably, as represented in FIG. 2, the first surface portion is a portion of the shoulder 205 of the tyre 200. Preferably, the entire remaining portion of the side wall 204 of the tyre 200 remains undeformed. As an example, the compression force is such as to deform the portion of side wall 204 so that the maximum excursion, taken between all of the points of said portion of side wall, between the position in the absence of forces and the deformed position, the excursion being measured along the direction of the compression force, is equal to a value comprised between about 10 and about 20 mm.

The device 10 in the compact configuration of FIG. 9b can come substantially close to the deformation element 130 (again see FIG. 2) to illuminate and acquire images of the first surface portion of tyre 200 deformed by the deformation element 130. The processing unit 180 controls the robotic arm 220 to bring the first light source 110 towards the surface of the tyre 200 and the deformation element 130, so that a linear surface portion inside the first deformed portion at least partially coincides with or is close to the lens line 106 in the focal plane 121. The linear portion also belongs, at least partially, to the first deformed surface portion on the side of the deformation element 130. Preferably, the distance between deformation element 130, and in particular the thrusting roller and the device 10 is comprised between about 30 mm and about 50 mm.

The processing unit 180, therefore, controls the movement member of the support 102 to set the tyre 200 in rotation.

As a function of the angular position signal received by the encoder, with the rotation of the tyre in progress, the drive and control unit 140 cyclically activates in rapid sequence the first light source 110 and the linear camera 105 to acquire a respective two-dimensional digital image (in colour or monochromatic) of the respective linear surface portion in synchrony with the activation of the first light source 110. The control unit 140 will control in parallel the switching on of the source elements 113 of the first light source 110 that work in synchrony with the linear camera 105. The two source elements 113 therefore switch on at the same time.

More preferably, the drive and control unit 140 controls the first light source 110 to emit a diffused radiation on the first surface portion 202 of the tyre 200, for example at a predetermined frequency. Such a stroboscopic frequency is for example equal to 0.1 ms. The drive and control unit 140, furthermore, controls the camera 105 to acquire an image of the first surface portion illuminated by the first light source in synchrony with the illumination thereof. Therefore, an image of the first surface portion of tyre 200 illuminated is acquired by the camera 105 each time the first light source 110 that illuminates the portion with diffused light is switched on.

Once the desired rotation of the tyre 200 has been carried out to examine the desired surface portion, preferably at least one complete rotation to acquire the entire circular extension, a digital image of a tyre "ring" is obtained, made with all of the digital images of the sequence of linear portions each illuminated with the first light source. For a complete 360° image for example 25,000 single linear images are used.

Optionally, a third portion of the surface of the tyre is selected, preferably but not necessarily again belonging to the sidewall 204 of the outer surface thereof, but distinct—at least partially—from the first portion. The deformation element 130 can thus be positioned, preferably again through the processing unit of the apparatus 180, at a distinct surface portion of the tyre 200, so as to deform a second surface portion of the tyre, including the selected third portion. In this way, a new analysis can be carried out, bringing the device 10 towards the new position so as to obtain an illumination of the further deformed outer surface portion of the tyre. See for example the difference between the position of the deformation element 130 in FIG. 2 and in FIG. 3 and the consequent different position of the device 10 in the two figures: in FIG. 2 an outer surface portion of shoulder 205 of the tyre is illuminated by the first light source 110, whereas in FIG. 3 an outer surface portion of the central area 207 of the sidewall 204 of the tyre 200 is illuminated by the first light source 110. Moreover, in FIG.

2, the rotation axis 117 of the thrusting roller, positioned at the shoulder 205, is inclined with respect to the plane defined by the support of the tyre 200, whereas in FIG. 3 the rotation axis 117 of the thrusting roller is substantially perpendicular to the rotation axis 201, thus parallel to the aforementioned plane defined by the support 102 of the tyre 200.

Furthermore, a second portion of the outer surface of the tyre 200 to be checked is selected. Preferably, but not necessarily, this second portion belongs to the bead 206 of the tyre 200.

The processing unit 180 controls the deformation element 130 to move away from the surface of the tyre so that no deformation force is applied on it. Moreover, the unit 180 controls the pistons 15, 16 so as to take the second light source 108 into the operative configuration of FIGS. 9a, 10, 11 and 5. Furthermore, the processing unit 180 controls the robotic arm 220 to take the device 10 towards the second surface portion, part of the bead of the tyre, and controls the movement member of the support 102 to set the tyre 200 in rotation. The configuration reached is represented in FIGS. 4 and 4a.

The first light source 110 and the second light source 108 are also controlled by the drive and control unit 140 to emit a radiation on the second surface portion 202 of the tyre 200. Preferably, the first light source 110 emits diffused radiation on the second surface portion, whereas the second light source 108 emits grazing radiation, coming from opposite half-spaces with respect to the optical plane 107 thanks to the provision of the two sub-sources 109a and 109b. Preferably, all of the light sources emit light radiation to illuminate the second surface portion of tyre, for example at a predetermined frequency. Such a stroboscopic frequency is for example equal to 0.064 ms. Preferably, the light sources, i.e. the first light source 110, the first sub-light source 109a and the second sub-light source 109b, are switched on alternately, i.e. in a given time period only the first source 110 or the first sub-source 109a or the second sub-light source 109b of the second source 108 illuminates the second surface portion of tyre. The drive and control unit 140, furthermore, preferably controls the camera 105 so as to acquire an image of the second surface portion illuminated by the first source or by the first sub-source or by the second sub-light source in synchrony with the illumination thereof. Therefore, advantageously, the camera 105 acquires an image of the second surface portion of tyre 200 illuminated each time the first light source 110 is switched on, which illuminates the portion with diffused light, an image of the second surface portion of tyre 200 illuminated every time the first sub-light source 109a is switched on, which illuminates the second portion with grazing light from one side of the optical plane 107 and an image of the second surface portion of tyre 200 illuminated every time the second sub-light source 109b is switched on, which illuminates the second portion with grazing light from the other side of the optical plane 107. In this way, advantageously, for every second surface portion three distinct images to be processed are acquired in which the same portion is illuminated with a radiation having distinct characteristics. In this way, it is possible to acquire both an image in diffused light and two images in grazing light of the same surface portion. These three images can also form distinct portions of a single two-dimensional image, in which a first portion is obtained with the grazing light, a second portion with grazing light from a first direction of the optical plane (for example from the right) and a third portion with grazing light from a second opposite direction of the optical plane (for example from the left).

Preferably, each image is a linear image.

Preferably, the apparatus comprises an encoder (not shown) to detect the angular position of the support, the drive and control unit being configured to activate said first light source 110, and second light source 108, and to control the detection system as a function of an angular position signal of the support sent by the encoder.

As an example, the time difference between the acquisition of the first and second linear image, as well as between the second and third linear image and then cyclically between the first and third linear image, is less than 0.2 milliseconds.

Therefore, for substantially the same surface portion three linear images are obtained, each with a different illumination.

The expression "substantially said surface portion", or, later on, "substantially a same surface portion", mean that the first and second or third light source illuminate two (or three) respective surface portions that can be spatially shifted from one another but are comparable according to the present invention, i.e. show the same elements substantially in the same position. For example the two (or three) surfaces can be shifted, on the plane of the surface itself, by a distance of less than 0.2 mm, preferably less than, or equal to, 0.1 mm. Advantageously, said distance is less than, or equal to, the linear dimension of surface associated with a pixel (the latter as an example being equal to 0.1 mm), in the case in which the detection system includes a camera, for example matrix or linear. In other words, each pixel of the first image shows a micro-surface portion that is less than 0.2 mm away from the micro-surface portion shown by the pixel of the second image corresponding to each said pixel.

In other words, the three images can be substantially overlapped pixel by pixel, although the real linear surface portion associated with a single linear image does not coincide exactly for the three images, due to the rotation of the tyre that has occurred in the meantime. However, the choice of the acquisition frequency of the images and of the rotation speed is such that the three images are interlaced and thus comparable pixel by pixel. Advantageously, each pixel of the first (or second or third) image shows a micro-surface portion that differs from the micro-surface portion shown by the pixel of the second (or respectively third or first) image corresponding to each said pixel apart from the linear surface dimension associated with a pixel, as an example the spatial shift being equal to about one third of a pixel. In this way, the three images are interlaced and the acquisition of the three linear images takes place in a time period during which the tyre has rotated by a portion equal to a pixel (as an example equal to about 0.1 mm).

Once the desired rotation of the tyre has been carried out to examine the desired surface portion, preferably at least one complete rotation to acquire the entire circular extension, a single digital image is obtained that is made with all of the digital images of the sequence of linear portions each illuminated with a respective light source. The processing unit 180 receives such an image from the detection system 104 and extracts the corresponding first, second and third image of the entire desired surface portion therefrom.

In the case in which a single image is acquired as described above formed from a portion with diffused light [A], a portion with grazing light dx [B] and a portion with left grazing [C], a succession repeated until the entire tyre is acquired, an overall image is obtained formed by the sequence ABCABCABCABCABCABCAB-CABCABC . . . . In processing this image is divided into three effective images, obtaining AAAAAAAA . . . BBBBBBBB . . . CCCCCCCC . . . .

Preferably, the processing unit 180 is also configured for the following functions: receiving the images acquired from the linear camera 105; and processing the images in order to check the surface portion. The processing unit 180 comprises for example a PC or a server. Preferably, the processing unit 180 is adapted for processing the second and third image to be processed obtained with grazing light by comparing them in order to obtain information on an altimetric profile of the surface portion. Preferably, the comparison between the second and third image to be processed comprises calculating a difference image in which each pixel is associated with a value representative of the difference between the values associated with the corresponding pixels in the second and third image to be processed.

Preferably, before comparing the second and third image to be processed it is foreseen to equalise the second and third image to be processed, for example equalising the average luminosity thereof globally or locally.

Preferably, the processing unit 180 processes the first image to be processed in diffused light to detect the possible presence of defects on the surface portion, using the information obtained by the aforementioned comparison between the second and third image to be processed.

Preferably, the processing unit 180 is configured to calculate the difference between the second and the third image in order to obtain information on an altimetric profile (e.g. possible presence or absence of projections and/or depressions) of the linear surface portion.

Preferably, calculating the difference between the second and third image comprises calculating a difference image in which each pixel is associated with a value representative of the difference between the values associated with the corresponding pixels in the second and third image. In this way it is possible to use the image obtained from the difference between the second and third image to highlight the three-dimensional elements (such as the raised pitting on the inner surface of the tyre or the raised writing) and take into account such information in the processing of the image in diffused light to look for defects.

The invention claimed is:

1. A method for checking a tyre, comprising:
   providing a tyre to be checked;
   associating a first light source and a second light source with a camera, the first and second light source being independently activatable;
   applying a first force against a first surface portion of the tyre to generate a first deformed surface portion while keeping the second light source deactivated;
   illuminating the first deformed surface portion with a first light radiation emitted by the first light source;
   acquiring, through the camera, a first image of the first deformed surface portion illuminated by the first light radiation;
   removing the first force from the first surface portion of the tyre;
   selecting a second surface portion at least partially distinct from the first surface portion of the tyre, the second surface portion being undeformed;
   illuminating the second surface portion of the tyre with a second light radiation emitted by the second light source;
   acquiring, through the camera, a second image of the second surface portion illuminated by the second light radiation; and
   processing the first image and the second image for detection of possible defects in the first surface portion and in the second surface portion of the tyre,
   wherein:
   the second light source comprises a first sub-light source emitting a first sub-light radiation and a second sub-light source emitting a second sub-light radiation,
   for each point of the second surface, the first sub-light radiation and the second sub-light radiation respectively originate from two opposite half-spaces with respect to an optical plane of the camera, and
   the illuminating of the second surface portion comprises
      illuminating the second surface portion with the first light radiation at a first time,
      illuminating the second surface portion with the first sub-light radiation at a second time different from the first time, and
      illuminating the second surface portion with said second sub-light radiation at a third time different from the first time and the second time.

2. The method according to claim 1, further comprising: arranging the first sub-light source and the second sub-light source symmetrically with respect to the first light source.

3. The method according to claim 1, wherein illuminating with the first light radiation comprises illuminating the first surface portion or the second surface portion with a diffused first light radiation.

4. The method according to claim 1, wherein illuminating with the second light radiation comprises illuminating the second surface portion with a first grazing sub-light radiation or a second grazing sub-light radiation.

5. The method according to claim 1, wherein providing the tyre comprises:
   arranging the tyre on a support plane with an axial mid-plane of the tyre substantially parallel to the support plane, thereby defining a resting side portion and a free side portion of the tyre arranged at a certain height with respect to the support plane.

6. The method according to claim 1, wherein the first force comprises a force component in a direction of a rotation axis of the tyre.

7. The method according to claim 6, wherein the force component is in a direction towards the mid-plane.

8. The method according to claim 1, further comprising: bringing the first light source to the first deformed surface portion at a distance ranging from about 25 mm to about 55 mm.

9. The method according to claim 1, further comprising: bringing the first light source to the second surface portion at a distance ranging from about 25 mm to about 55 mm.

10. The method according to claim 1, further comprising: applying a second force against a third surface portion of the tyre to generate a second deformed surface portion, the third surface portion being at least partially distinct from the first surface portion and from the second surface portion;
    illuminating the second deformed surface portion with the first light radiation emitted by the first light source; and acquiring, through the camera, a third image of the second deformed surface portion illuminated by the first light radiation.

11. The method according to claim 10, wherein the first surface portion or the third surface portion belongs to the free side portion of the tyre.

12. The method according to claim 10, wherein illuminating of the third surface portion with the first light radiation comprises illuminating the third surface portion with a diffused first light radiation.

13. The method according to claim 10, wherein the first surface portion or the third surface portion is a surface portion of a sidewall or of a shoulder of the tyre.

14. The method according to claim 13, wherein the second surface portion is a surface portion of a bead of the tyre.

15. The method according to claim 10, wherein:
applying of the first force or the second force against the first surface portion of the tyre or against the third surface portion of the tyre to generate the first deformed surface portion or the second deformed surface portion comprises keeping the first deformed surface portion or the second deformed surface portion at a predetermined height with respect to the support plane of the tyre.

16. The method according to claim 15, wherein the height depends on a model of the tyre.

17. The method according to claim 1, wherein illuminating of the second surface portion comprises:
illuminating the second surface portion with the first light radiation at a first time; and
illuminating the second surface portion with the second light radiation at a second time different from the first time.

18. The method according to claim 1, wherein acquiring the second image comprises:
acquiring a first image to be processed when the second portion is illuminated by the first light radiation;
acquiring a second image to be processed when the second portion is illuminated by the first sub-light radiation; and
acquiring a third image to be processed when the second portion is illuminated by the second sub-light radiation.

19. The method according to claim 18, wherein:
at least one of the first image, the second image, and the third image comprises a plurality of linear images of a succession of linear surface portions, contiguous to one another or partially overlapping, and
the plurality of linear images being acquired on a linear portion of the succession of linear portions that is respectively illuminated, in an alternate sequence, by the first light radiation, the first sub-light radiation, and the second sub-light radiation.

20. The method according to claim 18, wherein:
at least one of the first image and the third image comprises a plurality of linear images of a succession of linear surface portions, contiguous to one another or partially overlapping, and
the plurality of linear images being acquired on each linear portion of the succession of linear portions illuminated by the first light radiation.

21. The method according to claim 1, further comprising:
rotating the tyre about a rotation axis of the tyre; and
illuminating the tyre in a plurality of angular positions of the tyre to obtain a plurality of first images or second images or third images at respective different angular positions of the tyre.

22. The method according to claim 21, wherein applying of the first force comprises applying a constant pressure to the first deformed surface of the tyre during the step of rotating the tyre.

23. The method according to claim 22, wherein a value of the constant pressure is based on a type of the tyre.

24. The method according to claim 1, wherein at least 75% of a total light power of the second light radiation incident on each point of the second surface portion, forms a first angle of incidence with respect to a plane tangent to the surface of the tyre at the each point, that is less than or equal to 55°.

25. The method according to claim 1, wherein:
when deactivated, the second light source is controlled not to emit the second light radiation and is positioned at a distance from a focal plane of the camera that is greater than a distance of the first light source from the focal plane,
when activated, the second light source emits the second light radiation and is positioned at a distance from the focal plane that is equal to or less than a distance of the first light source from the focal plane, and
before illuminating the second surface portion, the second light source is controlled to switch from being deactivated to being activated.

26. The method according to claim 1, wherein the first light source is adapted for emitting diffused light radiation and the second light source is adapted for emitting grazing light radiation.

* * * * *